United States Patent
Benchikh et al.

(10) Patent No.: US 9,434,687 B2
(45) Date of Patent: Sep. 6, 2016

(54) DETECTION OF SYNTHETIC CANNABINOIDS

(75) Inventors: Elouard Benchikh, Crumlin (GB); Stephen Peter FitzGerald, Crumlin (GB); Paul John Innocenzi, Crumlin (GB); Philip Andrew Lowry, Crumlin (GB); Ivan Robert McConnell, Crumlin (GB)

(73) Assignee: Randox Laboratories Limited, Crumlin (GB)

( * ) Notice: Subject to any disclaimer, the term of this patent is extended or adjusted under 35 U.S.C. 154(b) by 560 days.

(21) Appl. No.: 13/585,646

(22) Filed: Aug. 14, 2012

(65) Prior Publication Data

US 2013/0066053 A1    Mar. 14, 2013

Related U.S. Application Data

(63) Continuation-in-part of application No. 13/332,042, filed on Dec. 20, 2011, now Pat. No. 8,906,633.

(30) Foreign Application Priority Data

Feb. 14, 2011  (GB) .................................. 1102544.2
Jun. 21, 2011  (GB) .................................. 1110425.4

(51) Int. Cl.
  *C07K 16/16*   (2006.01)
  *C07D 209/12*  (2006.01)
  *C07K 16/44*   (2006.01)
  *C07K 17/14*   (2006.01)

(52) U.S. Cl.
  CPC ............ *C07D 209/12* (2013.01); *C07K 16/44* (2013.01); *C07K 17/14* (2013.01)

(58) Field of Classification Search
  None
  See application file for complete search history.

(56) References Cited

U.S. PATENT DOCUMENTS

| | | | |
|---|---|---|---|
| 5,817,766 A | 10/1998 | Hui et al. | |
| 6,900,236 B1 * | 5/2005 | Makriyannis et al. | 514/415 |
| 8,906,633 B2 * | 12/2014 | Benchikh et al. | 435/7.1 |
| 2013/0065323 A1 | 3/2013 | Benchikh et al. | |
| 2013/0196354 A1 * | 8/2013 | Fitzgerald et al. | 435/7.92 |
| 2015/0118763 A1 | 4/2015 | Fitzgerald et al. | |

FOREIGN PATENT DOCUMENTS

| | | |
|---|---|---|
| EP | 0736529 A1 | 3/1996 |
| EP | 2487155 A1 | 8/2012 |
| WO | 02073214 A2 | 9/2002 |
| WO | 2010127452 A1 | 11/2010 |

OTHER PUBLICATIONS

Dresen et al., "Monitoring of herbal mixtures potentially containing synthetic cannabinoids as psychoactive compounds," J. Mass Spectrometry, 2010, vol. 45, issue 10, pp. 1186-1194, Article first published online: Sep. 20, 2010.*

Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Zhao et al., "Synthesis of Phenol, Aromatic Ether, and Benzofuran Derivatives by Copper-Catalyzed Hydroxylation of Aryl Halides," Angew. Chem. Int. Ed., 2009, vol. 48, issue 46, pp. 8729-8732.*
C. V. Rao, "Immunology,. A textbook", Alpha Science Internatl. Ltd., 2005, pp. 63, 69-71.*
De Jager, A.D. et al., "LC-MS/MS Method for the Quantitation of Metabolites of Eight Commonly-Used Synthetic Cannabinoids in Human Urine—An Australian Perspective," Journal of Chromatography B, 2012, vol. 897, pp. 22-31.
Hudson, S. et al., "Use of High-Resolution Accurate Mass Spectrometry to Detect Reported and Previously Unreported Cannabinomimetics in 'Herbal High' Products," J. Anal. Toxicol., 2010, vol. 34, pp. 252-260.
Huffman, J. et al., "1-Pentyl-3-Phenylacetylindoles, a New Class of Cannabimimetic Indoles," Bioorganic & Medicinal Chemistry Letters, 2005, vol. 15, pp. 4110-4113.
Kraemer, T. et al., "V10—Studies on the Metabolism of JWH18, the Pharmacologically Active Ingredient of Different Misused Incenses," Saarland University, Abstracts—Vortrage Hauptsymposium, 2008, vol. 76, No. 2, pp. 90.
Liu, Y. et al., "Design and Synthesis of AX4697, a Bisindolylmaleimide Exo-Affinity Probe that Labels Protein Kinase C Alpha and Beta," Bioorganic & Medicinal Chemistry Letters, 2008, vol. 18, pp. 5955-5958.
Melvin, L.S. et al., "A Cannabinoid Derived Prototypical Analgesic," J. Med. Chem., 1984, vol. 27, No. 1, pp. 67-71.
Moller, I. et al., "Screening for the Synthetic Cannabinoid JWH-018 and its Major Metabolites in Human Doping Controls," Drug Testing Analysis, 2011, vol. 3, pp. 609-620.
Rana, S. et al., "Routine Screening of Human Urine for Synthetic Cannabinoids by LC-MS/MS Utilizing Spectrum Based Library Search," Redwood Toxicology Laboratory, SOFT 2010 Annual Meeting, Richmond, Virginia, Abstract.
Rao, C.V., "Immunology, A Textbook," Alpha Science International Ltd., 2005, pp. 63, 69-71.
Singh, P. et al., "Synthesis and Evaluation of Indole-based New Scaffolds for Antimicrobial Activities—Identification of Promising Candidates," Bioorganic & Medicinal Chemistry Letters, 2011, vol. 21, pp. 3367-3372.
Sobolevsky, et al., "Detection of JWH-018 Metabolites in Smoking Mixture Post-Administration Urine," Forensic Science International, 2010, vol. 200, Issues 1-3, pp. 141-147.
Uchiyama, N. et al., "Chemical Analysis of Synthetic Cannabinoids as Designer Drugs in Herbal Products," Forensic Science International, 2010, vol. 198, pp. 31-38.
Weissman, A. et al., "Cannabimimetic Activity from CP-47,497, a Derivative of 3-Phenylcyclohexanol," J. Pharmacol. Exp. Ther, 1982, vol. 223, No. 2, pp. 516-523.
Wild, D. (editor), The Immunoassay Handbook, Third Edition, Elsevier Ltd., 2005, pp. 255-256.

(Continued)

*Primary Examiner* — Galina Yakovleva
(74) *Attorney, Agent, or Firm* — Saul Ewing LLP; Kathryn Doyle; Domingos J. Silva

(57) ABSTRACT

The invention describes methods and kits for detecting and determining current and future synthetic cannabinoids from the JWH and CP families. Unique antibodies derived from novel immunogens enable said methods and kits.

1 Claim, 15 Drawing Sheets

(56) References Cited

OTHER PUBLICATIONS

Wintermeyer, A. et al., "In vitro Phase I Metabolism of the Synthetic Cannabimimetic JWH-018," Anal. Bioanal. Chem., 2010, vol. 398, pp. 2141-2153.

Randox Toxicology, Product List 2012, pp. 1-43.

Watanabe, K., et al., "Cross-Reactivity of Various Tetrahydrocannabinol Metabolites with a Monoclonal Antibody against Tetrahydrocannabinolic Acid," Journal of Health Science, (2000), vol. 46, No. 4, pp. 310-313.

Tanaka, H., et al., "Monoclonal antibody against tetrahydrocannabionolic acid distinguishes *Cannabis sativa* samples from different plant species," Forensic Science International (1999), vol. 106, pp. 135-146.

Salamone, S., et al., "A Non-Cannabinoid Immunogen Used to Elicit Antibodies with Broad Cross-Reactivity to Cannabinoid Metabolites," Journal of Forensic Sciences, pp. 821-826, 1998, v. 43, No. 4.

Tanaka, H., "Immunochemical Approach Using Monoclonal Antibody against •9-TetrahydrocannabinolicAcid (THCA) to Discern Cannabis Plants and to Investigate New Drug Candidates," Current Drug Discovery Technologies, (2011) vol. 8, pp. 3-15.

Dresen, S., et al., "Development and validation of a liquid chromatography—tandem mass spectrometry method for the quantitation of synthetic cannabinoids of the aminoalkylindole type and methanandamide in serum and its application to forensic samples," J. Mass Spectrom, (2011), vol. 46, pp. 163-171.

Logan, B., et al., "Technical Bulletin: NMS Labs test for JWH-018, JWH-019, JWH-073, JWH-250 and AM-2201 Primary Monohydroxy Metabolites in Human Urine," NMS Labs, (2011), pp. 1-5.

Logan, B., et al., "Identification of Synthetic Cannabinoids in Herbal Incense Blends in the United States," Forensic Sciences, (2012), vol. 57, No. 5, pp. 1168-1180.

\* cited by examiner

R = Methyl    JWH-015

R = Ethyl     JWH-016

R = Propyl    JWH-007

Hapten-E

US 9,434,687 B2

DETECTION OF SYNTHETIC CANNABINOIDS

This application is a continuation-in-part of U.S. patent application Ser. No. 13/332,042 entitled Detection of Synthetic Cannabinoids, filed Dec. 20, 2011, which claims priority to Great Britain Patent Application Nos. 1102544.2 and 1110425.4. Each of these applications are hereby incorporated by reference.

BACKGROUND

The increasing rise in the use of stealth drugs (novel synthetic drugs that were previously or remain analytically/structurally uncharacterised and unclassified by government institutions), is exemplified by synthetic cannabinoid products which incorporate JWH-018 as the active ingredient. Stealth synthetic cannabinoid (SSC) drug manufacturers can base their choice of active molecular target on scientific literature studies that address the therapeutic potential of $CB_1$ (the CNS cannabinoid receptor) agonists and antagonists. By incorporating novel, analytically uncharacterised compounds with high $CB_1$ receptor affinity into herbal mixtures (packaged under such names as Spice, Yucatan Fire), the manufacturers are able to legally target drug consumers clandestinely by promoting the material as herbal therapeutics. A problem for governments and drug enforcement agencies is that even after identifying and banning a new synthetic cannabinoid, the manufacturers can rapidly react to the banning by incorporating a different active analogue into the same or a different herbal product; targeted minor changes in the molecular structure of the known active compound can preserve receptor activity but often produces a molecule whose GC-MS/LC-MS (the commonly applied detection techniques) profile is completely different from the original active molecule. Hence the new active molecule initially remains unidentified and a further resource intensive and costly chemical analytical study to enable structural characterisation is required. The main active ingredients highlighted in SSC products to date are JWH-018, CP 47,497 and JWH-073 (Uchiyama et al. 2010; Hudson et al. 2010; Dresen et al. 2010). Initial studies of the metabolism of JWH compounds have highlighted metabolic processes similar to tetrahydrocannabinol (THC) metabolism, namely ring and alkyl substituent hydroxylation, carboxylation and glucuronidation. As described herein, unless otherwise stated, JWH refers to molecules comprising structure I which are $CB_1$-active or metabolites of the $CB_1$-active parent, in which the indole ring system is present as a fused heterobicyclic i.e. it is not part of, for example, a fused heterotricyclic ring system. Y can be hydrogen or a substituted or unsubstituted alkyl group such as butyl, pentyl or 2-(morpholin-4-yl)ethyl, while R is a carbon atom which may be part of a fused or unfused, substituted or unsubstituted aromatic ring or a substituted or unsubstituted alkyl, alkenyl or alkynyl chain optionally attached to a fused or unfused, substituted or unsubstituted aromatic ring, but is usually a substituted or unsubstituted naphthyl ring.

Structure I

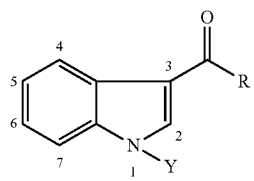

Indolyl, naphthyl, carboxyalkyl, N-dealkylated and N-alkyl mono-, di-, and tri-hydroxylated metabolites, as well as their glucuronidated conjugates are reported JWH-018 metabolites (Sobolevsky et al. 2010; Kraemer et al. 2008). Moller et al. (2010) highlighted the same metabolites as Sobolevsky et al. (2010), with the monohydroxylated N-alkyl chain being the most abundant phase I metabolite; Wintermeyer et al. (2010) conducted an in vitro study that largely confirmed previous findings. Herbal therapeutics have been analysed using solvent extraction, pre-derivatisation and finally GC-MS analysis in SIM mode (Rana et al. 2010). This method is inadequate for the detection of future and 'current' JWH SSCs (it is conceivable that 'current' herbal therapeutics, as well as JWH-018, incorporate JWH a SSCs that are not yet characterised), requires sample pre-derivatisation, specialist staff for its implementation and expensive equipment. In order to address the problem associated with the cheap and rapid detection of known JWH molecules and their metabolites and/or future and associated metabolites based on the JWH drug families, the Inventors devised a novel method based on novel antibodies raised from novel immunogens. The antibodies underpin an effective analytical and economic solution to the detection and quantification of current and future JWH $CB_1$-active molecules in in vitro patient samples and herbal therapeutics.

SUMMARY OF THE INVENTION

The invention describes a rapid and practical method for the detection and determination of known and/or stealth synthetic cannabinoids based on the JWH drug family. Kits and their use for JWH SSC detection and determination in herbal therapeutics and in vitro patient samples are also described. The invention is underpinned by novel immunogens and antibodies which enable said methods, kits and applications.

DETAILED DESCRIPTION OF THE INVENTION

Figure 1:
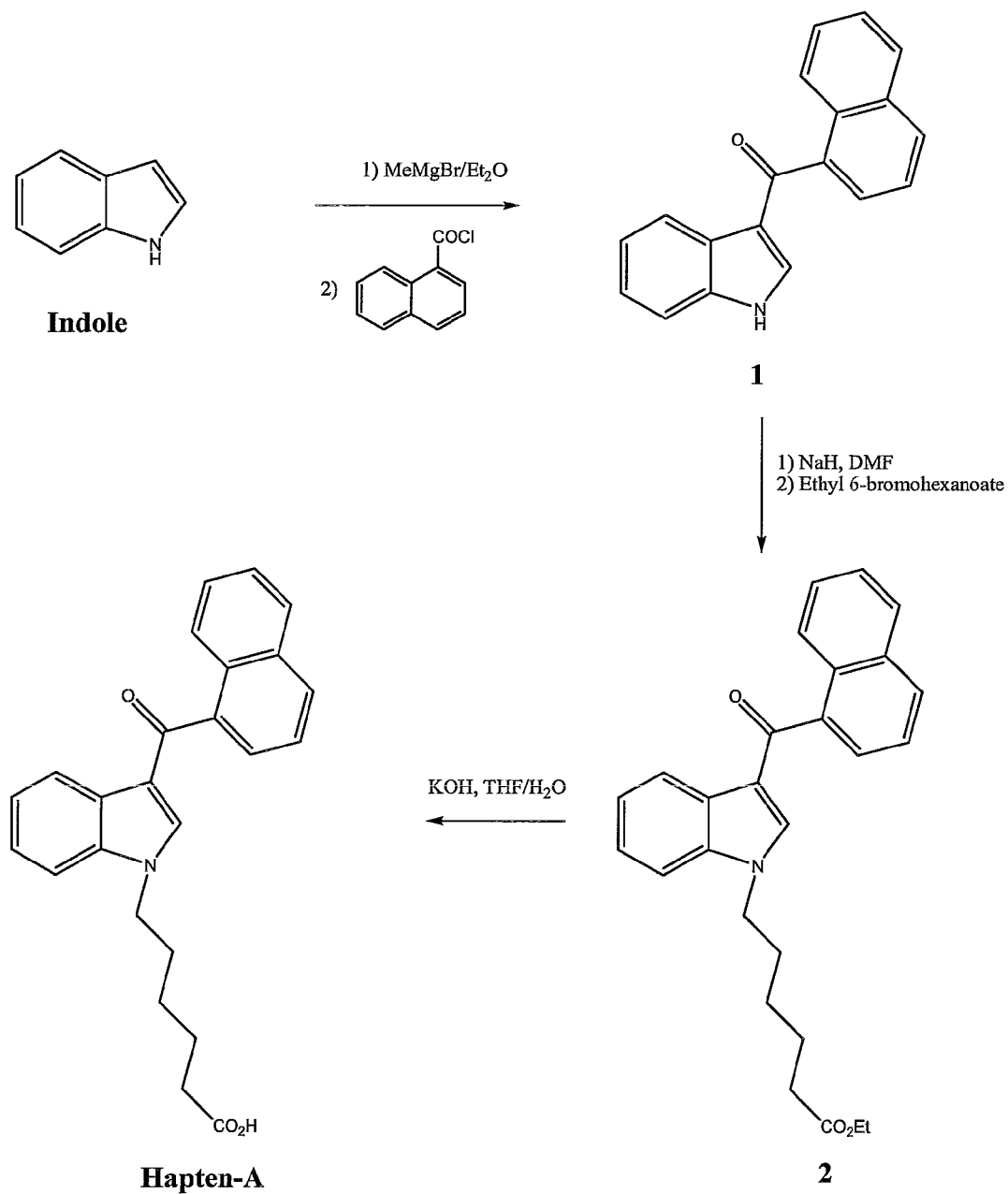
FIG. 1 shows a diagram of the synthesis of Hapten-A (used to generate Immunogen I).

A first aspect of the invention is an antibody raisable against one or more immunogens possessing the following structures

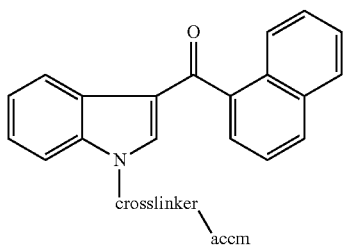
(a)

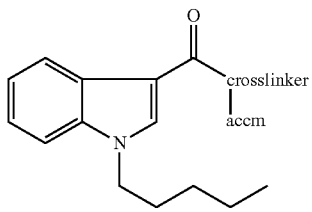
(b)

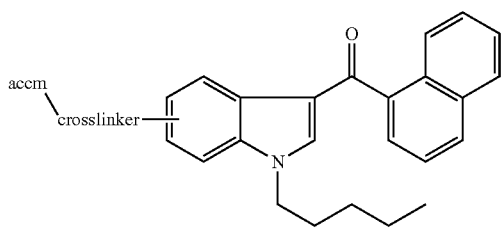
(c)

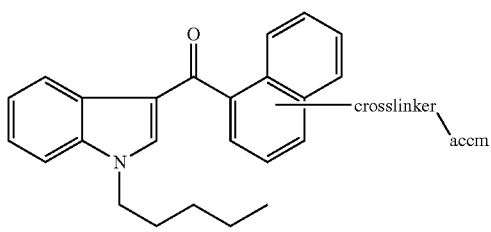
(d)

Group I (a)-(d) (Immunogens of the JWH Family)

in which the accm is an antigenicity conferring carrier material; the crosslinker is a functionalised linking group joining the accm to the remainder of the molecule and in which, in structure (a), the 2-position of the indole group can optionally be substituted with a methyl group.

The antibody may bind to an epitope of structure

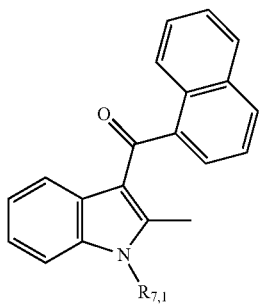

wherein,
$R_{7,1}$ is a $C_3$ or $C_4$ hydrocarbon chain. The antibody may bind to an epitope of the molecules JWH-015 and JWH-016. The antibody may be further characterised by being raisable from an immunogen of structure VII. Alternatively or additionally, the antibody may be further characterised by having a $B/B_0$ of ≤20% for all cross-reactants listed in Table 10 as having a $B/B_0$ below the indicated cut-off (standardised with RCS-4 and using tracer ESC6585).

The antibody may bind to an epitope of structure

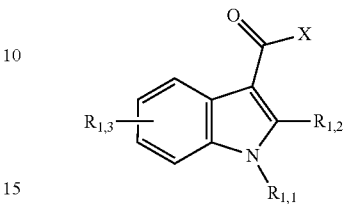

wherein,
$R_{1,1}$ is H or a $C_1$ to $C_6$, substituted or unsubstituted, saturated, hydrocarbon chain;
$R_{1,2}$ is H or methyl, optionally H;
$R_{1,3}$, if present, is methoxy or OH; and
X is a substituted or unsubstituted naphthyl moiety, optionally an unsubstituted naphthyl moiety, or a substituted benzyl moiety. Optionally, $R_{1,1}$ is selected from H; substituted methyl, substituted ethyl, substituted or unsubstituted propyl, substituted or unsubstituted butyl, substituted or unsubstituted pentyl or hexyl; wherein $R_{1,1}$ is, optionally, selected from (1-methyl-2-piperidinyl)methyl, ethyl-morpholino, propyl, substituted propyl selected from 1,2-dimethylpropyl, 2,2-dimethylpropyl or butyryl; butyl, substituted butyl selected from valeryl, 1-methylbutyl, 2-metylbutyl, 3-methylbutyl, 3-hydroxybutyl, 4-hydroxybutyl, pentyl, substituted pentyl selected from 4-hydroxypentyl, 5-hydroxypentyl, 5-fluoropentyl, 4-fluoropentyl and 4-hydroxy-5-fluoropentyl, 4-pentenyl and hexyl. Optionally, $R_{1,3}$, if present, is present at one of positions 5, 6 or 7 of the indole ring, optionally, at one of positions 6 or 7 of the indole ring. Further optionally, when X is substituted naphthyl, the naphthyl is substituted at the 6-position of the naphthyl ring with, optionally, methyl or, when X is substituted phenyl, the phenyl is substituted at position 2 of the phenyl ring with, optionally, iodine. The antibody may be characterised by being raisable from an immunogen of structure I. The antibody may be further characterised by having a $B/B_0$ of ≤16% for all cross-reactants listed in Table 10 as having a $B/B_0$ below the indicated cut-off (standardised with JWH-018 and using tracer ESC6557).

The antibody may bind to an epitope of structure

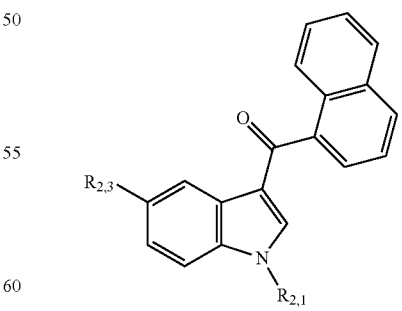

wherein,
$R_{2,1}$ is $C_4$ to $C_6$, substituted or unsubstituted, saturated or unsaturated, hydrocarbon chain; and
$R_{2,3}$ is H or hydroxyl. Optionally, $R_{2,1}$ is selected from butyl, pentyl, substituted pentyl selected from 4-fluoropentyl and 5-fluoropentyl, 4-pentenyl and hexyl. The antibody may be further characterised by having been derived from an immunogen of structure II. Alternatively or additionally, the antibody further characterised by having a B/B₀ of ≤15% for all cross-reactants listed in Table 10 as having a B/B₀ below the indicated cut-off (standardised with JWH-018 and using tracer ESC6557).

The antibody may bind to an epitope of structure

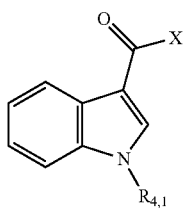

wherein,
$R_{4,1}$ is a $C_4$ or $C_5$, substituted or unsubstituted, saturated or unsaturated, hydrocarbon chain;
Y is substituted or unsubstituted naphthyl moiety or substituted phenyl moiety, in which Y is optionally a substituted naphthyl moiety. Optionally, $R_{4,1}$ is selected from butyl, substituted butyl selected from 3-methylbutyl; pentyl; substituted pentyl selected from 4-fluoropentyl and 5-fluoropentyl; and 4-pentenyl. Optionally, Y is substituted naphthyl and the naphthyl is substituted with methyl, ethyl, propyl, methoxy or chlorine, optionally at one of positions 4, 5, 6 or 7 of the naphthyl ring. Further optionally, Y is substituted phenyl, the phenyl is substituted with methoxy or iodine, optionally at position 2 of the phenyl ring and $R_{4,1}$ is selected from pentyl and 5-fluoropentyl. Further optionally, Y is substituted naphthyl and the naphthyl is substituted with methyl or methoxy at position 4 of the naphthyl ring and $R_{4,1}$ is pentyl. The antibody may be further further characterised by being raisable from an immunogen of structure IV. Alternatively or additionally, the antibody may be characterised by having a B/B₀ of ≤15% for all cross-reactants listed in Table 10 as having a B/B₀ below the indicated cut-off (standardised with JWH-018 and using tracer ESC5913).

The antibody may bind to an epitope of structure

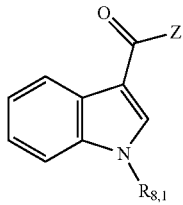

wherein,
$R_{8,1}$ is a $C_4$ or $C_5$, substituted or unsubstituted, hydrocarbon chain;
Z is substituted or unsubstituted 1- or 2-naphthyl, adamantyl, substituted benzyl or substituted phenyl moiety. Optionally, $R_{8,1}$ is selected from butyl; pentyl; and substituted pentyl, optionally selected from 5-fluoropentyl, 4-fluoropentyl and 4-hydroxypentyl. Optionally, when Z is substituted 1- or 2-naphthyl, the naphthyl is substituted with methyl or methoxy, optionally at the a B/B₀ below the indicated cut-off (standardised to JWH-018 and using tracer ESC57944 position on the naphthyl ring or, when Z is substituted benzyl, the benzyl is substituted with methyl optionally at the ortho or meta positions on the phenyl ring, methoxy or chlorine or, when $R_3$ is substituted phenyl, the phenyl is substituted with methoxy optionally at the meta or para positions of the phenyl ring or iodine. The antibody may be further characterised by being raisable from an immunogen of structure VIII. Alternatively or additionally, the antibody of may be characterised by having a B/B₀ of ≤20% for all cross-reactants listed in Table 10 as having a B/B₀ below the indicated cut-off (standardised to JWH-018 and using tracer ESC5794).

By functionalised, it is meant the crosslinker incorporates atoms that enable it to bond to both the accm and the JWH moiety, forming a bridging group. In structure (c) the crosslinker extends from the 4, 5, 6 or 7-position of the indole ring and in structure (d) the crosslinker extends from the 2, 3, 4, 5, 6, 7, or 8-position of the naphthyl ring. The crosslinker concept is well known to the person skilled in immunogen synthesis. For the current invention, when conjugating the hapten to the accm to form the immunogen, the nature and length of the crosslinker follows standard methods in order to optimise hapten epitopic recognition by the antibody. This entails a crosslinker of low immunogenicity and a chain length preferably of no greater than about ten atoms, most preferably no greater than six atoms.

Preferably for structure (a) the crosslinker is —(CO)ₙ-D-Y— and where n=0 or 1, and D is a $C_{1-10}$, preferably a $C_{1-5}$ substituted or unsubstituted straight chain alkylene or arylene moiety and Y, which is attached to the accm, is selected from groups such as carbonyl, amino, thiol, maleimide, isocyanato, isothiocyanato, aldehyde, diazo and dithiopyridyl. Y is preferably carbonyl or amino Optionally, the 2-position on the indole ring may be substituted with methyl.

Preferably for structures (b), (c) and (d), the crosslinker is -(A)ₙ-(D)ₚ-Y— where A=O, —N(R)—, S, —S(O)— (sulphoxide) or —S(O)₂— (sulphonyl) and R=H or $C_{1-5}$ alkyl, n=0 or 1, p=0 or 1 and D is a $C_{1-10}$, preferably a $C_{1-5}$ substituted or unsubstituted straight chain alkylene or arylene moiety and Y, which is attached to the accm, is selected from groups such as carbonyl, amino, thiol, maleimide, isocyanato, isothiocyanato, aldehyde, diazo and dithiopyridyl. Y is preferably carbonyl or amino.

Preferred immunogens correspond to structures (a) and (c). The crosslinker of structure (c) of Group I is preferably attached to the 5-indole position. The crosslinker of structure (d) of Group I is preferably attached to the 4-naphthyl position. It has been found that immunogens of the invention raise antibodies that are able to bind to several JWH molecules and metabolites. The skilled person is aware that for these antibodies to recognize JWH molecules they must bind to particular structures or epitopes of the hapten (in this context the hapten being that part of the immunogen that is not the crosslinker or accm); the epitopes are often distinct groups incorporating functional groups.

For example, with reference to the JWH immunogen of structure (a) of Group I, the epitope recognized by the antibody will be all or part of the 3-(1-naphthoyl)-1H-indole moiety.

For an immunogen of structure (b) of Group I the epitope recognized by the antibody will be all or part of the N-pentyl-3-carbonyl-1H-indole moiety.

The accm can be any material that makes all or part of the hapten susceptible to antibody recognition and binding. For example the accm can be a protein, a protein fragment, a synthetic polypeptide or a semi-synthetic polypeptide.

Especially preferred immunogens of the invention correspond to structures (a) and (c) of Group I in which structure (a) has Y=carbonyl, n=0 and D=pentylene and structure (c) has Y=carbonyl, A=O, n=1 and D=methylene.

A further aspect of the invention is an antibody raised against an immunogen of structure (a), (b) or (c) of Group I, that is able to bind to molecules of the JWH family and their metabolites that comprise structure I. The term 'able to bind to', as used herein, does not imply that the antibodies have a choice of whether or not to bind to the JWH molecules, but that under standard immunoassay conditions the antibodies will bind to the JWH molecules.

Figure 6:
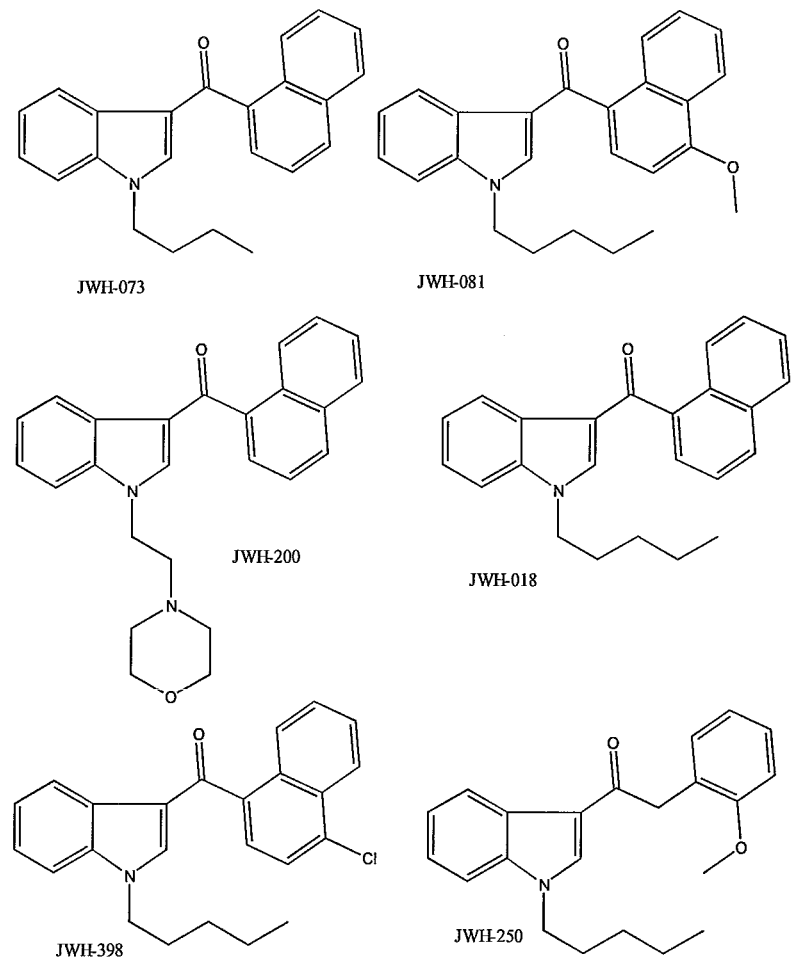
FIG. 6 contains diagrams of representative molecules of the JWH family.
Figure 7:
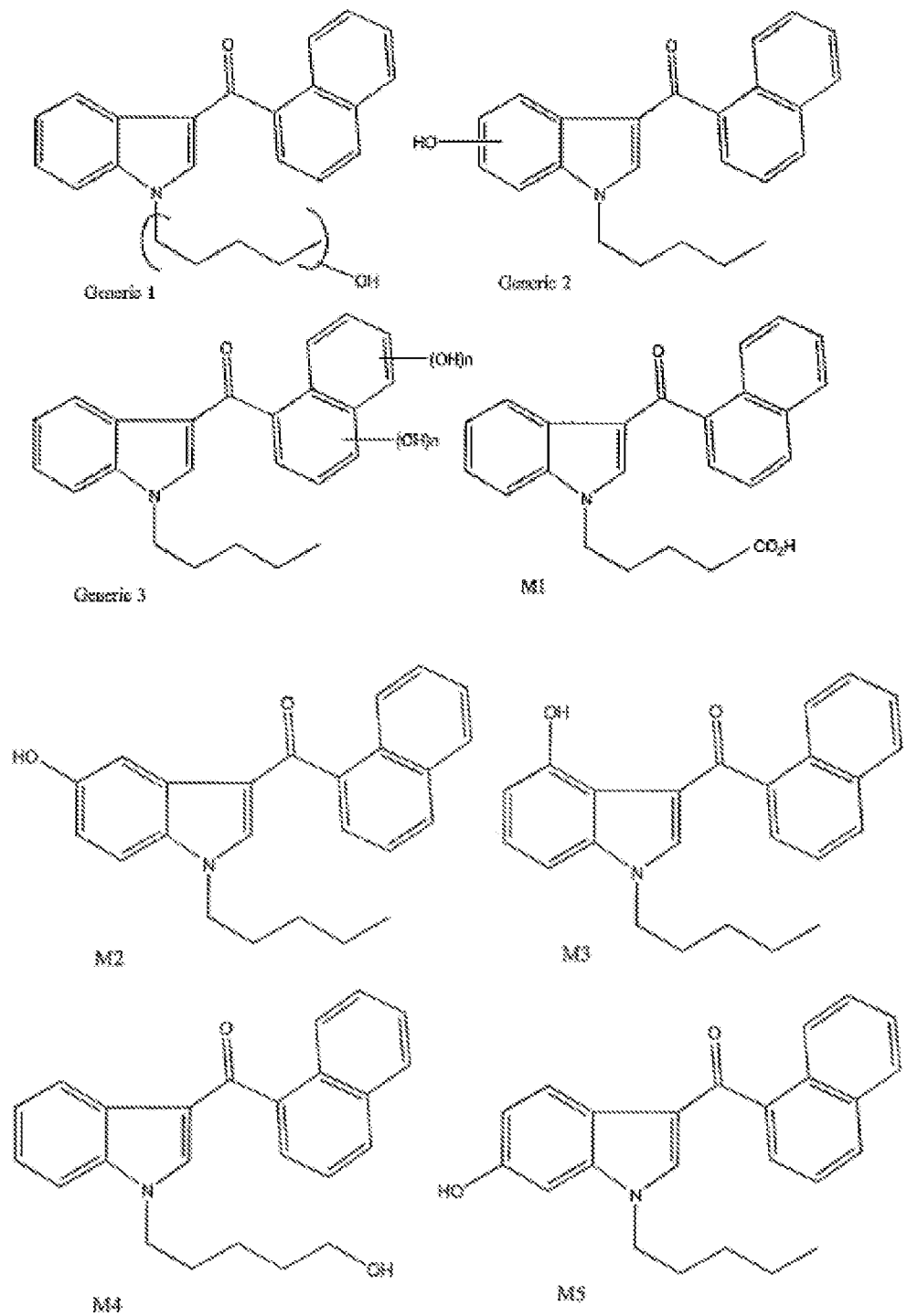
FIG. 7 Identified and hypothesised metabolites of JWH (n=1-2). The hydroxylated metabolites are potentially further metabolised to the corresponding glucuronide(s).
Figure 8:
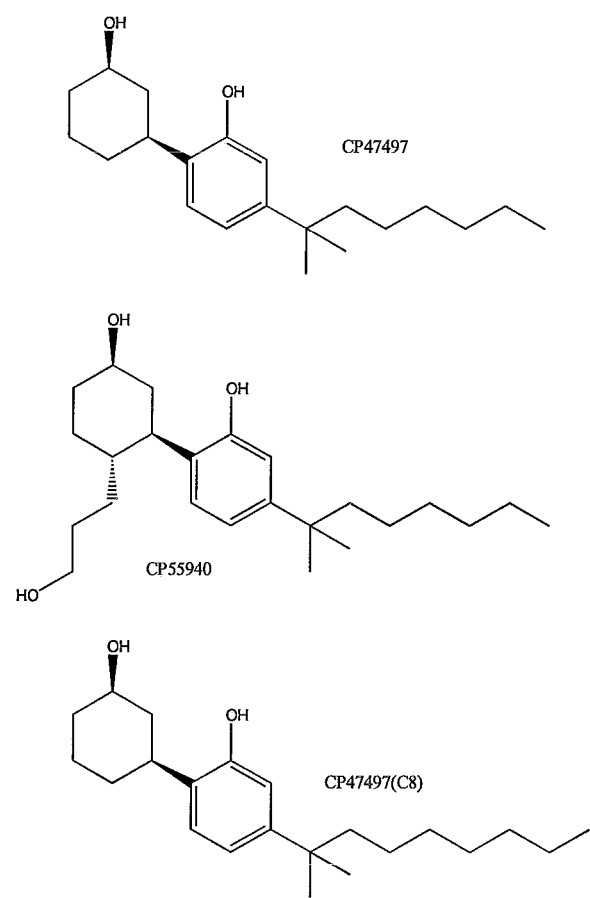
FIG. 8 contains diagrams of CB 1-active molecules of the CP family (available from Cayman Chemical Company, 1180 East Ellsworth Road, Ann Arbor, Mich. 48108, USA).
Figure 9:
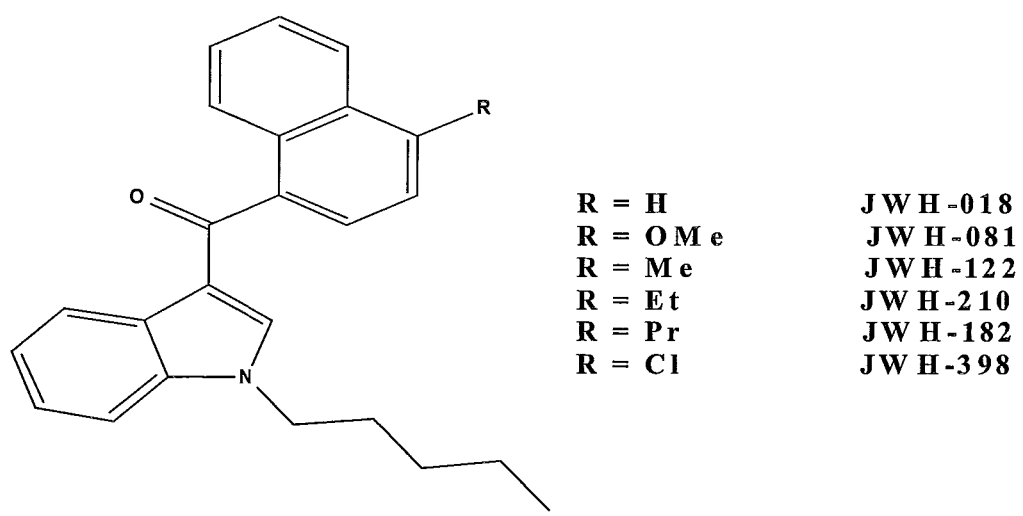
FIG. 9 contains diagrams of chemical structures of JWH-081, JWH-018, JWH-122, JWH-210, JWH-182 and JWH-398.
Figure 10:
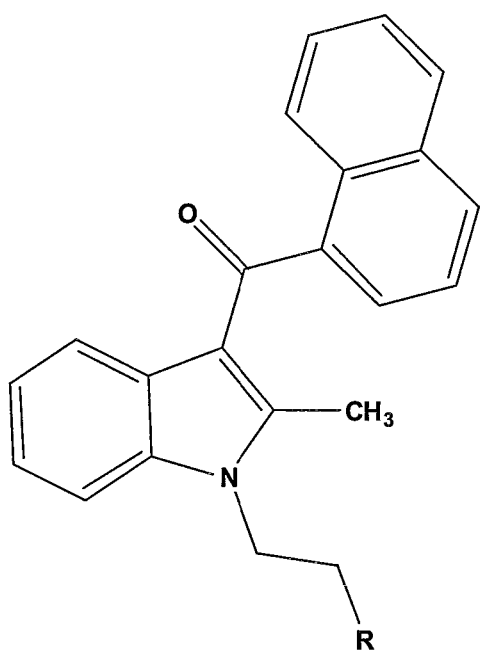
FIG. 10 contains diagrams of chemical structures of JWH-015, JWH-016 and JWH-007.
Figure 11:
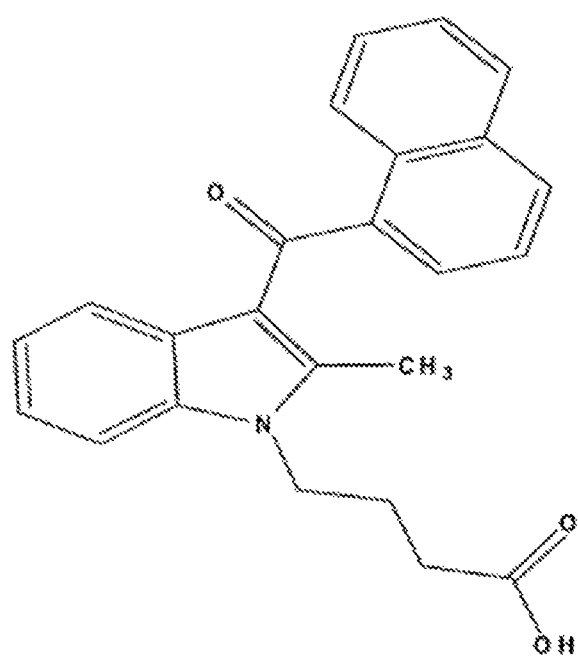
FIG. 11 contains diagrams of chemical structures of Hapten-E.

The antibodies are preferably raised against immunogens of structure (a) or (c) of Group I, the antibodies being able to bind to several molecules and metabolites of the JWH family, including JWH-018 and its N-alkyl hydroxylated metabolites. It is especially preferred that the antibodies are raised from structure (a) of Group I in which Y=carbonyl, n=0 and D=pentylene and structure (c) of Group I in which Y=carbonyl, A=O, n=1 and D=methylene, the antibodies able to bind to several molecules and metabolites of the JWH family, including JWH-018 and its dealkylated, hydroxylated and carboxylated metabolites, JWH-073, JWH-081, JWH-200 and JWH-398. Preferably, the antibodies raised against immunogens of structure (a) or (c) of Group I are also able to bind to one or more metabolites of JWH-018 identified as M1-M5 in FIG. 7, namely JWH-018 N-pentanoic acid metabolite (M1), JWH-018 5-hydroxyindole metabolite (M2), JWH-018 4-hydroxyindole metabolite (M3), JWH-018 N-(5-hydroxypentyl) metabolite (M4) and JWH-018 6-hydroxyindole metabolite (M5); and/or the JWH-018 metabolite JWH-018 N-(4-hydroxypentyl) metabolite; and/or the 5-fluoropentyl derivative of JWH-018, 1-(5-fluoropentyl)indol-3-yl (1-naphthyl) methanone; and/or the JWH-018 metabolite identified as JWH-250 in FIG. 6; and/or one or more JWH-073 metabolites selected from JWH-073 N-(3-hydroxybutyl) metabolite and JWH-073 N-(4-hydroxybutyl) metabolite. These compounds are available from, for example, Cayman Chemical Company. The antibodies also have the potential to bind to $CB_1$-active derivatives of JWH molecules that could represent future generations of SSCs.

Optionally, the antibodies may have broad cross-reactivity across the JWH family and metabolites. For example, without intending to limit the invention thereto, antibodies raised to Immunogen I (structure (a) of Group I) may be specific to JWH-018 N-(5-hydroxypentyl) metabolite (M4) and cross-reactive to JWH-073, JWH-200, JWH-018, JWH-018 N-pentanoic acid metabolite (M1), JWH-018 5-hydroxyindole metabolite (M2), JWH-018 4-hydroxyindole metabolite (M3), JWH-018 6-hydroxyindole metabolite (M5) and 3-(1-naphthoyl)-1H-Indole. Similarly, antibodies raised to Immunogen II (structure (c) of Group I) may be specific to JWH-018 6-hydroxyindole metabolite (M5) and cross-reactive to JWH-073, JWH-200, JWH-398, JWH-018, JWH-018 N-pentanoic acid metabolite (M1), JWH-018 5-hydroxyindole metabolite (M2), JWH-018 4-hydroxyindole metabolite (M3) and JWH-018 N-(5-hydroxypentyl) metabolite (M4).

Optionally, the antibodies raised to Immunogen I (structure (a) of Group I) will be able to bind to an epitope of JWH-073, JWH-200, JWH-018, JWH-018 N-pentanoic acid metabolite (M1), JWH-018 5-hydroxyindole metabolite (M2), JWH-018 4-hydroxyindole metabolite (M3), JWH-018 N-(5-hydroxypentyl) metabolite (M4) and JWH-018 6-hydroxyindole metabolite (M5). Optionally, the epitope will be all or part of 3-(1-naphthoyl)-1H-Indole.

Further optionally, the antibodies raised to Immunogen II (structure (c) of Group I) will be able to bind to an epitope of JWH-073, JWH-200, JWH-398, JWH-018, JWH-018 N-pentanoic acid metabolite (M1), JWH-018 5-hydroxyindole metabolite (M2), JWH-018 4-hydroxyindole metabolite (M3), JWH-018 N-(5-hydroxypentyl) metabolite (M4) and JWH-018 6-hydroxyindole metabolite (M5).

The invention also describes an antibody raised against an immunogen of structure (d), (e), (f) or (g) the antibody being able to bind to molecules of the CP family, metabolites of CP molecules and future SSC molecules comprising structure II. When used in reference to an antibody, the word specific in the context of the current invention refers to the analyte that is preferably bound by the antibody, as gauged by a suitable metric such as the $IC_{50}$. Given the $IC_{50}$ of various analytes their cross-reactivities can be calculated. The antibody can either be a polyclonal or monoclonal antibody using well-known methods. If the polyclonal antibody possesses the required specificity and sensitivity, that is, it binds a single analyte within the detection range of the assay, development of a monoclonal antibody is unnecessary. Alternatively, a polyclonal or monoclonal antibody that binds to several analytes might be desirable; in the context of the current invention antibodies that bind several analytes are preferred. One or more antibodies of the invention can be incorporated into a kit for the detection and determination of individual or multiple SSCs. The skilled person in the immunodiagnostic field is aware of several alternative immunoassay formats that could incorporate the antibodies of the invention either in solution or tethered (e.g. covalently bonded or electrostatically 'non-bonded' through van der waal's forces) to a solid substrate such as beads, glass/plastic slides or ceramic chips (a chip defined as a small, planar substrate). A preferred solid substrate onto which the antibodies of the invention are covalently bonded is a chip, preferably a ceramic chip; the word 'biochip' can be used to refer to a chip with antibodies attached. Such a "biochip" is described in EP1273349, incorporated herein by reference its entirety. Thus the invention also provides a solid substrate, preferably a biochip, comprising antibodies raised to an immunogen of one or more of structures (a), (b), (c), (d), (e), (f), (g) or (h), the antibodies being able to bind to an epitope of one or more molecules of the JWH family and/or CP family and/or one or more metabolites thereof. The antibodies of the invention can be used for the detection or determination of a single SSC such as JWH-018, either as the parent molecule or as a metabolite, but a preferred embodiment is the use of one or more antibodies, preferably two or more antibodies, at least one derived from Group I and one derived from Group II, for the detection or determination of several SSCs and/or their metabolites from the JWH and CP families. The detection and determination criteria for a SSC using an immunoassay platform includes, as is well-known in the art, exceeding a pre-defined cut-off/concentration value or measuring the calibrator equivalent value as derived from a calibrator curve (also referred to as a standard curve).

Classification of immunoassays depends on whether one (noncompetitive) or two (competitive) antigens are used:

1. Competitive, Homogeneous Immunoassay

The antigen in the unknown sample competes with labeled antigen to bind with antibodies. The amount of unbound, labeled antigen is then measured, which is directly proportional to the concentration of sample antigen.

2. Competitive, Heterogeneous Immunoassay

The antigen in the unknown sample competes with labeled antigen to bind with antibodies. The amount of labeled antigen bound to the antibody site is then measured. In this method, the response will be inversely related to the concentration of antigen in the unknown.

3. One-Site, Noncompetitive Immunoassay

The unknown antigen in the sample binds with labeled antibodies. The unbound, labeled antibodies are washed away, and the bound, labeled is measured, which is directly proportional to the amount of unknown antigen.

4. Two-Site, Noncompetitive Immunoassays

The antigen in the unknown sample is bound to the antibody site, then labeled antibody is bound to the antigen. The amount of labeled antibody on the site is then measured. It will be directly proportional to the concentration of the antigen because labeled antibody will not bind if the antigen is not present in the unknown sample. This type is also known as sandwich assay as the antigen is "sandwiched" between two antibodies.

Another aspect of the invention is a method of detecting or determining synthetic cannabinoids of the JWH family and their metabolites in an in vitro sample of an individual or in a solution derived from a substance suspected of containing synthetic cannabinoids comprising: contacting the sample or solution with one or more detecting agents and one or more antibodies of the invention that bind to molecules of the JWH family, measuring the detecting agents, and detecting or determining, by reference to calibrators, the presence or concentration of a molecule or molecules of the JWH family.

Optionally, the method further comprises a step of measuring the detecting agents before detecting or determining, by reference to calibrators, the presence or concentration of a molecule or molecules of the CP family. The detecting agents measuring step can be measuring detecting agent bound to the antibodies, the detecting agent being labeled antigen in a competitive, homogeneous immunoassay in which unbound, labeled antigen is measured. Alternatively, the detecting agents measuring step can be measuring detecting agent bound to the antibodies, the detecting agent being labeled antigen in a competitive, heterogeneous immunoassay in which bound, labeled antigen is measured. Further alternatively, the detecting agents measuring step can be measuring detecting agent bound to the antibodies, the detecting agent being labeled antibodies in a one-site, noncompetitive immunoassay in which bound, labeled antibodies are measured. Still further alternatively, the detecting agents measuring step can be measuring detecting agent bound to the antibodies, the detecting agent being labeled antibody that is bound to the antigen that is, in turn, also bound to the antibody.

With reference to 'detecting or determining', 'detecting' means qualitatively analyzing for the presence or absence of a substance, 'determining' means quantitatively analyzing for the amount of a substance.

Optionally, the detecting agent is a small molecule, generally of similar structure to a molecule to be detected conjugated to a labelling agent, the detecting agent being able to bind to one of the antibodies of the invention. The labelling agent is selected from an enzyme, a luminescent substance, a radioactive substance, or a mixture thereof. Preferably, the labelling agent is an enzyme, preferably a peroxidase, more preferably horseradish peroxidase (HRP). Alternatively, or additionally, the luminescent substance may be a bioluminescent, chemiluminescent or fluorescent material. For the purposes of the invention, the patient sample to be used for in vitro analysis can be hair or a peripheral biological fluid but is preferably whole blood, serum, plasma, or urine.

Preferably the synthetic cannabinoids to be detected or determined are one or more of JWH-018, JWH-073, JWH-200 and JWH-398 and the one or more antibodies are derived from immunogens of structures (a) and (c) of Group I. When referring to the detection or determination of a JWH molecule, with or without a suffixed number attached to JWH and CP, the metabolite or metabolites are also inferred unless otherwise stated.

The immunogen of structure (a) preferably has a crosslinker —X—Y— in which Y is carbonyl and is attached to the accm, and X is pentylene, and the immunogen of structure (c) has a crosslinker —O—CH2-C(O)— in which the carbonyl is attached to the accm.

Figure 5:
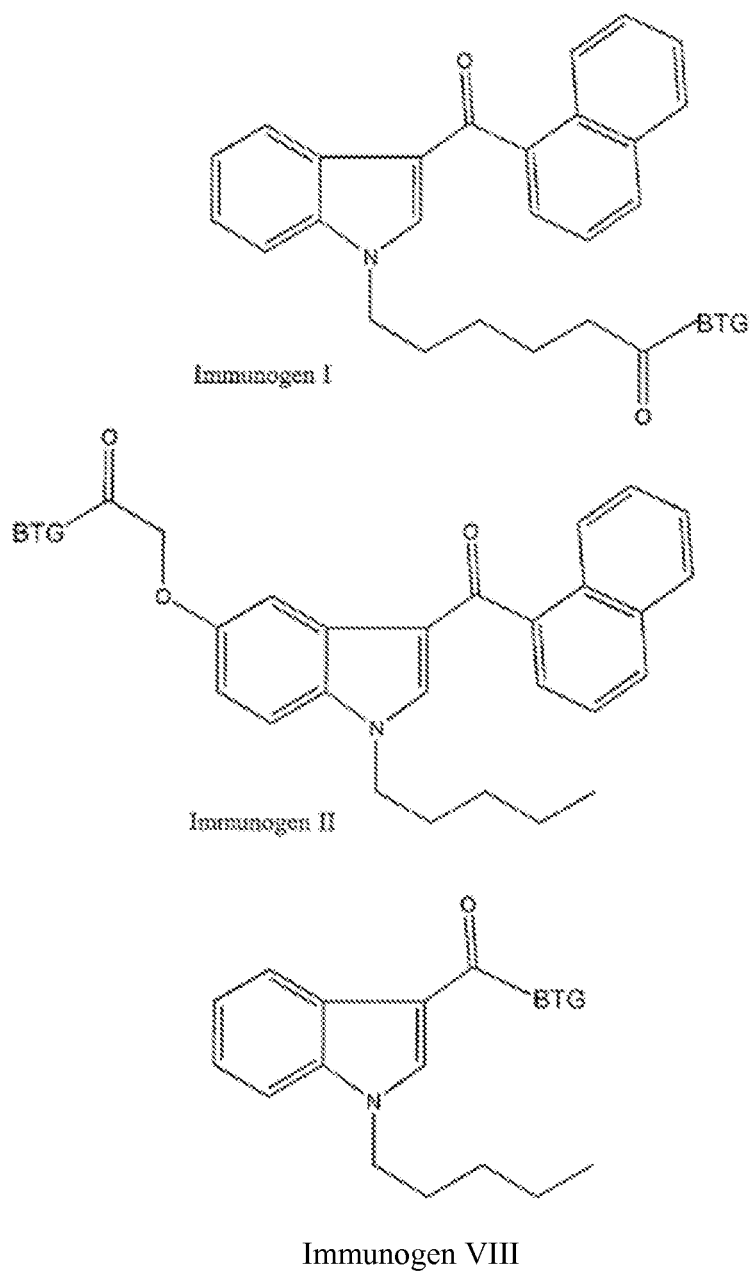
FIG. 5 contains diagrams of immunogens I, II and VIII.

The invention also describes kits for detecting or determining a molecule or molecules of the JWH family comprising one or more antibodies of the invention. Preferably, the kit comprises one or more antibodies raised to an immunogen of either structure (a), (b), (c) or (d) of Group I. More preferably the antibodies of the kit are derived from an immunogen of structure (a) and/or (c). A kit comprising antibodies derived from Immunogens I or II (FIG. 5) for detecting or determining one or more of JWH-018, JWH-073, JWH-200 and JWH-398 is particularly preferred. Optionally, the kit may comprise antibodies derived from Immunogens I or II for additionally or alternatively detecting or determining one of more of JWH-081, JWH-018 N-pentanoic acid metabolite (M1), JWH-018 5-hydroxyindole metabolite (M2), JWH-018 4-hydroxyindole metabolite (M3), JWH-018 N-(5-hydroxypentyl) metabolite (M4), JWH-018 6-hydroxyindole metabolite (M5), JWH-018 N-(4-hydroxypentyl) metabolite, 1-(5-fluoropentyl)indol-3-yl (1-naphthyl) methanone, JWH-250, JWH-073 N-(3-hydroxybutyl) metabolite and JWH-073 N-(4-hydroxybutyl) metabolite.

The antibodies of the kit are preferably tethered to any suitable solid support such as a chip. Although the solid support can be of any suitable shape such as a bead or a slide and of any suitable material such as silicon, glass or plastic, the solid support is preferably a ceramic chip. The kit may further include calibrators and one or more detecting agents and optionally includes instructions for the use of the antibodies of the kit and if incorporated, the calibrators and detecting agents, for detecting and determining molecules from the JWH CP family. The invention also embodies solid supports comprising the novel antibodies.

The antibodies of the invention are used for the detection or determination of JWH molecules either in herbal mixtures, an in vitro sample taken from an individual or any other substance suspected of their incorporation. A preferred use of the antibodies of the invention is their use in the detection and/or quantification of JWH-018, JWH-073, JWH-200 and JWH-398 in herbal mixtures and/or JWH-073, JWH-200, JWH-398 and JWH-018 and its metabolites in in vitro samples taken from individuals.

General Methods, Examples and Results

Preparation of Haptens, Immunogens and Detecting Agents

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and protein fragments. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen.

The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof.

Immunogen formation for the invention described herein involves conventional conjugation chemistry. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal using standard techniques. The signal emitted in the immunoassay is proportionate to the amount of detecting agent bound to the antibodies which in turn is inversely proportionate to the analyte concentration. The signal can be detected or quantified by comparison with a calibrator.

EXAMPLES

Preparation of Hapten A (See FIG. 1)

Example 1

Preparation of 3-(1-naphthoyl)-1H-indole 1

To a cooled solution of indole (5.85 g, 50 mmol) in ether (50 ml) under nitrogen was added slowly a solution of methylmagnesium bromide (3M) in ether (17.5 ml). After addition, the reaction mixture was warmed up to room temperature and stirred for 2 h at room temperature. Then the mixture was cooled down again to 0° C., and to it was added slowly with stirring a solution of 1-naphthoylchloride (9.5 g, 50 mmol) in ether (50 ml). The resulting mixture was warmed up to room temperature and stirred for 2 h at room temperature followed by slow addition of saturated ammonium chloride solution (375 ml). The mixture was then stirred overnight at room temperature. A white solid was formed, filtered, washed by ether and dried under high vacuum to give 3-(1-naphthoyl)-1H-Indole 1 (12.3 g, 91%).

Example 2

Preparation of N-(5-Ethoxycarbonylpentyl)-3-(1-naphthoyl)-1H-indole 2

To a suspension of sodium hydride (1.1 g, 30 mmol, 60% in mineral oil) in DMF (100 ml) under nitrogen was added solid 3-(1-naphthoyl)-1H-indole 1 (5.43 g, 20 mmol). After stirring at room temperature for 1 h, a solution of ethyl 6-bromohexanoate (6.6 g, 30 mmol) in DMF (10 ml) was added slowly with stirring over a period of 15 min and the mixture was then heated at 60° C. for 3 h. The solvent was removed under high vacuum and the crude product was suspended in water (150 ml) and extracted by ethyl acetate (2×150 ml). The combined ethyl acetate phases were washed by water (1×100 ml), brine (1×100 ml), dried over sodium sulphate filtered and concentrated to dryness. The crude product obtained was purified by chromatography on silica gel using hexane/ethyl acetate (8/2) to give the title compound 2 as an oil which became solid in the cold (7.1 g, 86%).

Example 3

Preparation of N-(5-carboxypentyl)-3-(1-naphthoyl)-1H-indole (Hapten-A)

To a solution of 2 (5.0 g, 12 mmol) in a mixture of THF/H2O (1:1) was added potassium hydroxide (1.7 g) and the mixture was stirred at 60° C. for 1 h. The THF was removed under vacuum, the aqueous solution acidified to pH 1 by the addition of hydrochloric acid solution (1N) and extracted by ethyl acetate (3×100 ml). The combined organic phases were washed by water (100 ml), brine solution (100 ml), dried over sodium sulphate, filtered and concentrated to dryness. The crude product obtained was dissolved in ethyl acetate (10 ml) and the Hapten-A precipitated by the addition of a mixture of ether/hexane as a white solid, filtered and dried under high vacuum to give Hapten-A (3.6 g, 78%).

Example 4

Conjugation of Hapten-A to BSA

To a solution of Hapten-A (52.2 mg, 0.13 mmol) in DMF (1.0 ml) was added N,N-dicyclohexylcarbodiimide (DCC) (34.0 mg, 0.16 mmol) and N-hydroxysuccinimide (19.0 mg, 0.16 mmol) and the mixture was stirred at room temperature overnight. The dicyclohexylurea formed was removed by filtration and the solution added dropwise to a solution of BSA (200 mg, 3.0 μmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 h at 4° C., and freeze-dried. MALDI results showed 9.83 molecule of Hapten-A had been conjugated to one molecule of BSA.

Example 5

Conjugation of Hapten-A to BTG (Immunogen I)

To a solution of Hapten-A (58.0 mg, 0.15 mmol) in DMF (1.0 ml) was added N,N-dicyclohexylcarbodiimide (DCC) (34.0 mg, 0.165 mmol) and N-hydroxysuccinimide (19.0 mg, 0.16 mmol) and the mixture was stirred at room temperature overnight. The dicyclohexylurea formed was removed by filtration and the solution was added dropwise to a solution of BTG (150 mg) in 50 mM sodium bicarbonate solution (pH 8.5) (10 ml). The mixture was then stirred overnight at 4° C. The solution was then dialysed against 50 mM phosphate buffer pH 7.2 (3 changes) for 24 h at 4° C., and freeze-dried to give Immunogen I.

Example 6

Conjugation of Hapten-A to HRP

EDC hydrochloride (10 mg) was dissolved in water (0.5 ml) and immediately added to a solution of Hapten-A (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP detecting agent was then dialysed overnight against 10 L of PBS at pH 7.2 at 4° C.

Figure 2:
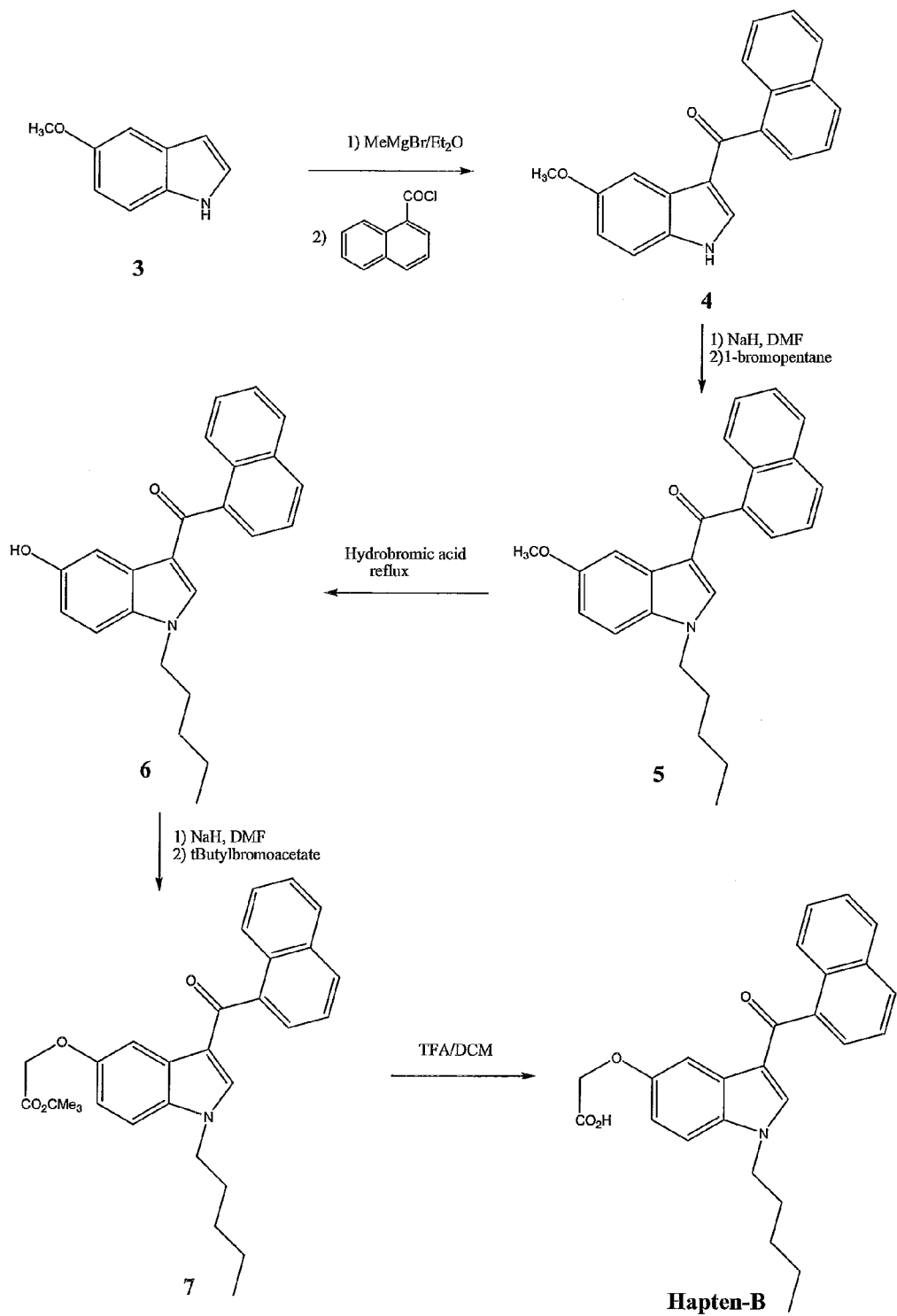
FIG. 2 shows a diagram of the synthesis of Hapten-B (used to generate Immunogen II).

Preparation of Hapten B (see FIG. 2)

Example 7

Preparation of 5-methoxy-3-(1-naphthoyl)-1H-indole 4

To a cooled solution at 0° C. of 5-methoxy-1H-indole 3 (7.4 g, 50 mmol) in diethyl ether (150 ml) under nitrogen was added dropwise a solution of methylmagnesium bromide (3M) in diethyl ether (17.5 ml) and the mixture was stirred for 2 h at room temperature. The solution was then cooled at 0° C. and to this solution was added a solution of 1-naphthoylchloride (9.5 g, 50 mmol) in diethyl ether (100 ml) dropwise over a period of 15 min. After the addition was completed the solution was warmed up at room temperature and stirred for 2 h followed by slow addition of saturated ammonium chloride solution (375 ml) and stirred overnight. The white solid formed was filtered, washed by ether and dried under high vacuum to give 5-methoxy-3-(1-naphthoyl)-1H-indole 4 (11.3 g, 75%).

Example 8

Preparation of 5-methoxy-3-(1-naphthoyl)-N-pentyl-1H-indole 5

To a suspension of sodium hydride (1.54 g, 45 7 mmol, 60% in mineral oil) in DMF (100 ml) under nitrogen was added dropwise a solution of 5-methoxy-3-(1-naphthoyl)-1H-indole 4 (9.83 g, 32.6 mmol) in DMF (50 ml) and the mixture was stirred at 40° C. for 1 h. The solution was then cooled to room temperature and to this mixture was added a solution of 1-bromopentane (8.2 g, 54.3 mmol) in DMF (25 ml). The mixture was stirred at 60° C. for 1 h. The solvent was removed under high vacuum and the crude product was suspended in water (200 ml) and extracted by ethyl acetate (2×200 ml). The combined ethyl acetate phases were washed by water (1×100 ml), brine (1×100 ml), dried over sodium sulphate, filtered and concentrated to dryness. The crude product obtained was purified by chromatography on silica gel using hexane/ethyl acetate (7/3) to give the title compound 5 as an oil which solidified upon cooling (7.1 g, 59%).

Example 9

Preparation of 5-hydroxy-3-(1-naphthoyl)-N-pentyl-1H-indole 6

To a solution of hydrobromic acid (48 w/w/%) in water (150 ml) was added 5 (6.5 g, 17.5 mmol) and the mixture was heated at reflux for 3 h. The solution was cooled to room temperature and concentrated to dryness. Water was then added (200 ml), the solution neutralized to pH 7-8 and then extracted with ethyl acetate (3×150 ml). The combined organic layers were washed by water (150 ml), brine (150 ml), dried over $Na_2SO_4$, filtered and concentrated to dryness. The crude product was then recrystallized from ethyl acetate/hexane to give a white solid of 5-hydroxy-3-(1-naphthoyl)-N-pentyl-1H-indole 6 (4.5 g, 72%).

Example 10

Preparation of 5-(tert-butoxycarbonylmethoxy)-3-(1-naphthoyl)-N-pentyl-1H-indole 7

To a suspension of sodium hydride (452 mg, 13 4 mmol, 60% in mineral oil) in DMF (25 ml) under nitrogen was added dropwise a solution of 6 (3.7 g, 10.35 mmol) in DMF (50 ml) and the mixture was stirred at 60° C. for 1 h. The solution was then cooled to room temperature and to this mixture was added a solution of tert-butyl bromoacetate (2.62 g, 13 4 mmol) in DMF (25 ml). The mixture was stirred at 60° C. for 3 h. The DMF was removed under high vacuum and the crude product was suspended in water (100 ml) and the mixture was extracted by ethyl acetate (2×100 ml). The combined ethyl acetate phases were washed by water (1×50 ml), brine (1×50 ml), dried over sodium sulphate filtered and concentrated to dryness. The crude product obtained was purified by chromatography on silica gel using hexane/ethyl acetate (9/1) to give the title compound 7 (3.5 g, 72%).

Example 11

Preparation of 5-carboxymethoxy-3-(1-naphthoyl)-N-pentyl-1H-indole (Hapten-B)

To a solution of 7 (3.0 g, 6 4 mmol) in dichloromethane (50 ml) was added TFA (25 ml) and the mixture was stirred at room temperature for 3 h. The mixture was evaporated to dryness and the crude obtained was purified by chromatography on silica-gel using 5% methanol in chloroform to give Hapten-B (2.1 g, 79%).

NMR $^{13}$C (CD$_3$OD, δ ppm): 194.55, 173.21, 156.53, 141.14, 140.15, 135.25, 134.10, 131.98, 131.17, 129.46, 128.9, 1127.85, 127.44, 126.87, 125.55, 125.85, 117.92, 115.14, 112.72, 106.33, 65.54, 30.59, 29.87, 23.2, 14.25

Example 12

Conjugation of Hapten-B to BSA

To a solution of Hapten-B (62.4 mg, 0.15 mmol) DMF (1.0 ml) was added N,N-dicyclohexylcarbodiimide (DCC) (34.1 mg, 0.16 mmol) and N-hydroxysuccinimide (19.02 mg, 0.16 mmol) and the mixture was stirred at room temperature overnight. The dicyclohexylurea formed was removed by filtration and the solution was added dropwise to a solution of BSA (200 mg, 3 μmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 h at 4° C., and freeze-dried. MALDI results showed 37.2 molecules of Hapten-B had been conjugated to one molecule of BSA.

Example 13

Conjugation of Hapten-B to BTG (Immunogen II)

To a solution of Hapten-B (56.0 mg, 0.13 mmol) in DMF (1.0 ml) was added N,N-dicyclohexylcarbodiimide (DCC) (30.6 mg, 0.14 mmol) and N-hydroxysuccinimide (17.1 mg, 0.14 mmol) and the mixture was stirred at room temperature overnight. The dicyclohexylurea formed was removed by filtration and the solution was added dropwise to a solution of BTG (150 mg) in 50 mM sodium bicarbonate solution (pH 8.5) (15 ml). The mixture was then stirred overnight at 4° C. The solution was then dialysed against 50 mM phosphate buffer pH 7.2 (3 changes) for 24 h at 4° C., and freeze-dried to give Immunogen II.

Figure 3:
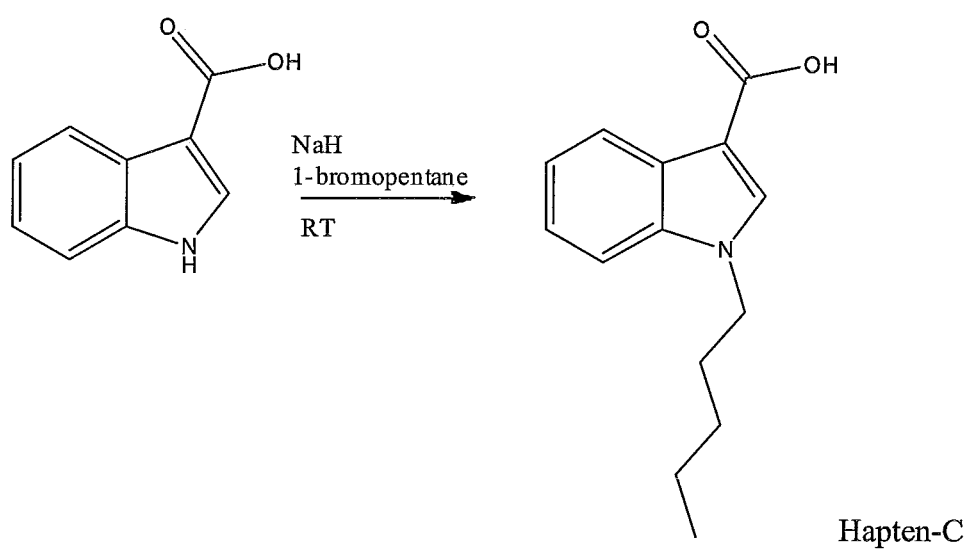
FIG. 3 shows a diagram of the synthesis of Hapten-C (used to generate Immunogen VIII).

Preparation of Hapten C (See FIG. 3)

Example 14

Preparation of 3-carboxy-1-pentyl-1H-indole (Hapten-C)

Indole 3-carboxylic acid (3 g, 18.62 mmol) was added to a suspension of sodium hydride (60% in oil) (1.11 g, 1.5 eq) in dry DMF (30 ml) under a nitrogen atmosphere. The mixture was stirred at room temperature for 45 min (H$_2$ evolving has ceased) and to this was added 1-bromopentane (4.62 ml, 2 eq) in dry DMF (10 ml) dropwise. The mixture was stirred at room temperature overnight. The solvents were removed in vacuo and to the residue was added water (30 ml) and ethyl acetate (30 ml). The ethyl acetate portion was separated, dried over sodium sulphate, filtered and evaporated to dryness. The crude residue was purified by column chromatography (silica gel: 20% ethyl acetate in hexane) to give the title compound (2.12 g, 49%) as a cream solid.

Example 15

Conjugation of 3-carboxy-1-pentyl-1H-indole (Hapten C) to BSA

To a solution of Hapten-C (26.13 mg, 0.113 mmol) in DMF (1.0 ml) was added N,N-dicyclohexylcarbodiimide (DCC) (25.64, 0.1243 mmol) and N-hydroxysuccinimide (14.30 mg, 0.1243 mmol) and the mixture was stirred at room temperature overnight. The dicyclohexylurea formed was removed by filtration and the solution was added dropwise to a solution of BSA (150 mg) in 100 mM sodium bicarbonate solution (pH 8.5) (9 ml). The mixture was then stirred overnight at 4° C. The solution was then dialysed against 50 mM phosphate buffer pH 7.2 (3 changes) for 24 hours at 4° C., and freeze-dried.

Example 16

Conjugation of 1-pentyl-1-H-indole-3-carboxylic acid (3-carboxy-1-pentyl-1H-indole, Hapten C) to BTG (Immunogen VIII)

To a solution of Hapten-C (31.22 mg, 0.135 mmol) in DMF (1.0 ml) was added N,N-dicyclohexylcarbodiimide (DCC) (30.74 mg, 0.149 mmol) and N-hydroxysuccinimide (17.1 mg, 0.149 mmol) and the mixture was stirred at room temperature overnight. The dicyclohexylurea formed was removed by filtration and the solution was added dropwise to a solution of BTG (150 mg) in 100 mM sodium bicarbonate solution (pH 8.5) (15 ml). The mixture was then stirred overnight at 4° C. The solution was then dialysed against 50 mM phosphate buffer pH 7.2 (3 changes) for 24 hours at 4° C., and freeze-dried to give Immunogen VIII.

Example 17

Conjugation of Hapten-B to HRP

EDC hydrochloride (10 mg) was dissolved in water (0.5 ml) and immediately added to a solution of Hapten-B (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP detecting agent was then dialysed overnight against 10 L of PBS at pH 7.2 at 4° C.

Example 18

Preparation of Antibodies to Immunogens I and II

Aqueous solutions of the immunogens prepared in examples 5 and 13 were formulated with Freund's Complete Adjuvant (FCA) to form emulsions consisting of 2 mg/ml Immunogen I and 2 mg/ml of Immunogen II in 50% (v/v) FCA. Three sheep were immunised with each emulsion (1° immunisations), 0.25 ml being intramuscularly injected at four sites in the rump of each animal. Subsequent immunisations (boosts 2-8) contained 1 mg/ml Immunogen I and 1 mg/ml Immunogen II. All boosts were emulsified in 50% (v/v) Freund's Incomplete Adjuvant (FIA) and administered to the appropriate sheep in the same manner as the 1° immunisations, at monthly intervals. Blood sampling took place 7-14 days after each boost. Each sample was processed to produce antiserum, which was further purified by caprylic acid and ammonium sulphate precipitation to yield an immunoglobulin (Ig) fraction. The Ig fraction was evaluated by competitive ELISA microtiter plate assay, as described in example 19 below.

Example 19

Development of Competitive ELISA for JWH Synthetic Cannabinoids and Metabolites (a) The wells of an enhanced binding 96 well polystyrene microtiter plate were coated with the Ig fraction of the antiserum raised to Immunogen I (Hapten A-BTG—example 5) and diluted in 10 mM Tris, pH8.5 (125 µl/well). The appropriate antibody coating concentration was determined using standard ELISA checkerboard techniques. The plate was incubated for 2 hours at 37° C., washed 4 times over a 10-minute period with Tris buffered saline containing Tween 20 (TBST) and tapped dry. Standard solutions of JWH synthetic cannabinoids, metabolites and selected molecules were prepared in TBST and 50 µl of each was added to the appropriate wells. 75 µl of conjugate (Hapten A-HRP) diluted in Tris buffer containing EDTA, D-mannitol, sucrose, thimerosal and BSA, was added to each of the wells. The appropriate dilution of conjugate was also determined using standard ELISA checkerboard techniques. The plate was incubated at 25° C. for 1 hour. The excess unbound conjugate was removed by washing 6 times over a 10-minute period with TBST and tapped dry. 125 µl of tetramethylbenzedine (TMB) substrate solution was added to each well of the plate that was then incubated for 15-20 minutes in the dark at room temperature. The reaction was terminated by addition of 125 µl of 0.2M sulphuric acid to each well. The absorbance was then measured at 450 nm using a microtiter plate reader.

Employing each series of standards, calibration curves were generated and these were used to determine the specificity of the immunoassay for the JWH synthetic cannabinoids, metabolites and selected molecules. The results of this study are presented in Tables 1 to 3, cross-reactivity being calculated according to the following formula:

% $CR = IC_{50, JWH-018}/IC_{50, CR} \times 100$

Where % CR is the percentage cross-reactivity, $IC_{50, JWH-018}$ is the concentration of JWH-018 that causes 50% displacement of signal and $IC_{50, CR}$ is the concentration of JWH synthetic cannabinoid/metabolite/selected molecule that causes 50% displacement of signal.

Table 1: Data generated from a competitive microtiter plate assay for JWH synthetic cannabinoids and metabolites, employing antiserum raised to Immunogen II (Hapten B-BTG) and conjugate (Hapten A-HRP) as detection reagent.

(b) In a similar manner to that described in Example 19(a), the wells of a 96 well microtiter plate were coated with the Ig fraction of the antiserum raised to Immunogen I (Hapten A-BTG). Conjugate (Hapten A-HRP) was employed as a detection reagent. The data generated is presented in Table 1.

Table 2: Data generated from a competitive microtiter plate assay for JWH synthetic cannabinoids and metabolites, employing antiserum raised to Immunogen I (Hapten A-BTG) and conjugate (Hapten A-HRP) as detection reagent.

(c) The resulting competitive ELISA for synthetic cannabinoids and metabolites was further employed to analyse urine and serum samples from 20 patients (Table 3).

(d) The resulting competitive ELISA for synthetic cannabinoids and metabolites was also employed to test for the 5-fluoropentyl derivative of JWH-018, (1-(5-fluoropentyl) indol-3yl (1-naphthyl) methanone (Table 4).

Results

TABLE 1

Antibody characterisation using antiserum raised to Immunogen II and detecting agent derived from Hapten-A in a competitive assay format (CR based on 100% for JWH-018)

| Analyte | $IC_{50}$ ng/ml | % Cross-reactivity |
| --- | --- | --- |
| JWH-018 | 2.11 | 100.00 |
| JWH-073 | 1.56 | 135.26 |
| JWH-398 | 17.55 | 12.02 |
| JWH-200 | 1.66 | 127.11 |
| 3-(1-naphthoyl)-1H-Indole | >>40 | <<5.28 |
| M1 | 5.48 | 38.50 |
| M2 | 1.62 | 130.25 |
| M3 | 9.16 | 23.03 |
| M4 | 1.15 | 183.48 |
| M5 | 0.98 | 215.31 |

>> implies a value greatly exceeding the value given (40 ng/ml was the highest concentration tested)
<< implies a value greatly below the value given

TABLE 2

Antibody characterisation using antiserum raised to Immunogen I and detecting agent derived from Hapten-A in a competitive assay format (CR based on 100% for JWH-018)

| Analyte | $IC_{50}$ ng/ml | % Cross-reactivity |
| --- | --- | --- |
| JWH-018 | 2.71 | 100.00 |
| JWH-073 | 0.93 | 291.40 |
| JWH-398 | >>40 | <<6.78 |
| JWH-200 | 0.31 | 874.19 |
| 3-(1-naphthoyl)-1H-Indole | 3.84 | 70.57 |
| M1 | 0.42 | 645.24 |
| M2 | 0.39 | 694.87 |
| M3 | 25.51 | 10.62 |
| M4 | 0.18 | 1505.56 |
| M5 | 2.04 | 132.84 |

>> implies a value greatly exceeding the value given (40 ng/ml was the highest concentration tested)
<< implies a value greatly below the value given

TABLE 3

Sensitivity and cross-reactivity (CR) of antibodies raised to Immunogens I & II of selected molecules

| Analyte | Standard Conc$^n$ ng/ml | $IC_{50}$ ng/ml | % CR |
| --- | --- | --- | --- |
| Serotonin | 750.00 | >750.00 | <0.28 |
| 4-Methoxypsilocin | 750.00 | >750.00 | <0.28 |
| Delta-9-THC | 750.00 | >750.00 | <0.28 |
| Cannabinol | 750.00 | >750.00 | <0.28 |
| 11-Hydroxy-δ-9-THC | 750.00 | >750.00 | <0.28 |
| CP 47,497 | 750.00 | >750.00 | <0.28 |
| 3-Carboxy-N-pentyl-1H-indole | 750.00 | >750.00 | <0.28 |
| 3-Carboxy-1H-indole | 750.00 | >750.00 | <0.28 |
| 3-Carboxymethyl-5-hydroxy-1H-indole | 750.00 | >750.00 | <0.28 |
| 5-Hydroxytryptophol | 750.00 | >750.00 | <0.28 |

TABLE 4

Sensitivity and cross-reactivity (CR) of antibodies raised to Immunogens I & II of JWH-018 and 1-(5-Fluoropentyl)indol-3-yl (1-naphthyl) methanone* (5-Fluoropentyl derivative)

| Immunogen | $IC_{50}$ ng/ml | | % Cross-reactivity |
|---|---|---|---|
| I | JWH-018 | 2.30 | 100.00 |
| I | 5-Fluoropentyl derivative | 0.02 | 11500.00 |
| II | JWH-018 | 1.97 | 100.00 |
| II | 5-Fluoropentyl derivative | 0.22 | 908.00 |

* Binding of this molecule to the $CB_1$ receptor is detailed in U.S. Pat. No. 6,900,236

Immunoassays using antibodies of the invention to test for potential cross-reactants (Table 3) and to screen the urine and serum of twenty patients for cross-reactive molecules, did not reveal any cross-reactants which could invalidate the measurements taken using the antibodies, methods, kits and products of the invention.

As can be seen from Tables 1 to 4, for the first time antibodies have been provided that bind to various JWH molecules, metabolites and potential metabolites, whereas other common indole-containing molecules and non-JWH $CB_1$-active molecules do not bind. The antibody produced from Immunogen I is able to bind to JWH molecules known to be incorporated in herbal therapeutics such as JWH-018, proposed metabolites such as M2 (Wintermeyer et al 2010), and potential metabolites such as M5. The detection and quantification of other JWH SSCs is also provided for, the antibodies of the invention bind a range of molecules comprising the 3-(1-naphthoyl)-1H-indole structure (e.g. JWH-071, JWH-398, M1 etc.). Table 3 confirms that the same antibodies do not cross-react with other psychoactive drugs, with molecules present in biological samples of patients who have not taken JWH containing substances or with molecules without the 3-(1-naphthoyl)-1H-indole such as 3-carboxy-1H-indole. The concept of using the antibodies of the invention to detect and determine future stealth synthetic cannabinoids is highlighted in Table 4; the 5-fluoropentyl derivative known to bind the CB 1 receptor, but which as of yet has not been detected in herbal therapeutics or similar substances, binds to antibodies raised from Immunogens I and II.

Figure 4:
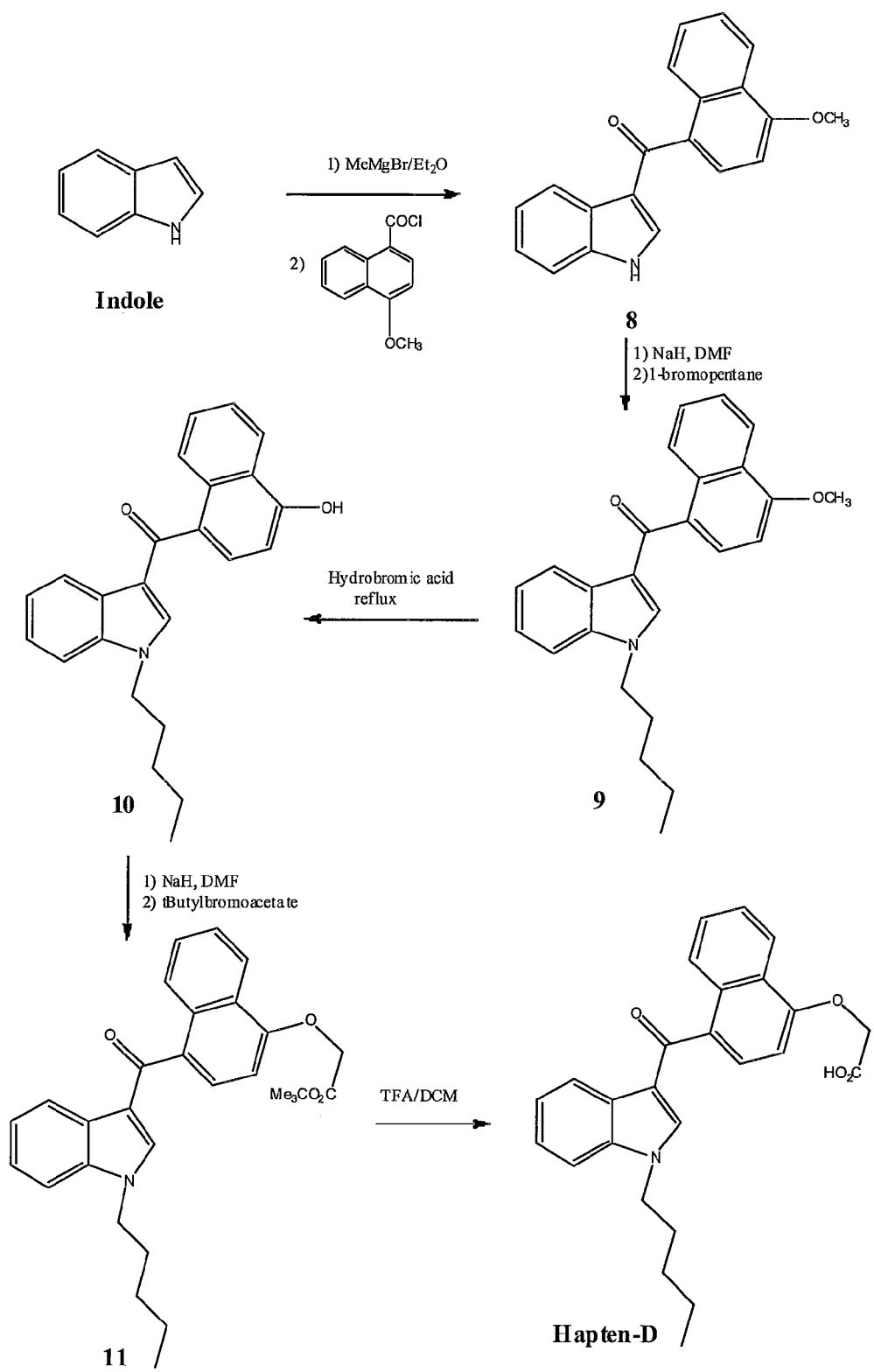
FIG. 4 shows a diagram of the synthesis of Hapten-D (used to generate Immunogen IV).

Preparation of Hapten D/Immunogen IV (see FIG. 4)

Example 20

Preparation of 4-methoxy-1-naphthoic acid

4-Methoxy-1-naphthaldehyde (10 g, 53.72 mmol) was dissolved in t-butanol (75 ml) and 2-methyl-2-butene (35 ml) was added at room temperature. A solution of sodium chlorite (7.99 g, 70.63 mmol) and sodium dihydrogen orthophosphate (9.15 g, 76.27 mmol) in water (50 ml) was added dropwise. The reaction mixture was stirred at room temperature overnight. The reaction mixture was concentrated in vacuo and the residue was washed with a solution of 2MHCl (100 ml) and the solid was filtered and washed with dichloromethane (100 ml) and water (100 ml) and dried in vacuo. The solid was recrystallised from methanol to give 5.95 g (55%) of 4-methoxy-1-naphthoic acid as cream crystals.

Example 21

Preparation of 3-(4-methoxy-1-naphthyoyl)indole 8

Indole (2.30 g, 19.65 mmol) was dissolved in diethylether (50 ml) under nitrogen atmosphere and cooled to 0° C. 3M MeMgBr solution (6.88 ml, 20.63 mmol) was added dropwise and allowed to stir at room temperature for 3 hours. In the meantime, 4-methoxy-1-naphthoic acid (3.97 g, 19.65 mmol) was dissolved in thionyl chloride (15 ml) and refluxed for 90 min, then the solvent was removed under vacuo and the residue was dissolved in diethylether (25 ml). The resulting solution was added dropwise to the indole reaction mixture at 0° C. and then allowed to stir at room temperature overnight. A solution of ammonium chloride (200 ml) was added to the reaction mixture and the resulting mixture was stirred at room temperature for 3 hours. The solid that was formed was collected by filtration, washed with water and hexane then air dried. The resulting solid was triturated with ether to give 4.78 g (81%) of 3-(4-methoxy-1-naphthyoyl)indole 8 as a cream solid.

Example 22

Preparation of 1-N-pentyl-3-(-4-methoxy-1-naphthyloyl)indole 9

3-(4-Methoxy-1-naphthyoyl)indole 8 (4.78 g, 15.86 mmol) was suspended in dimethylformamide (35 ml) and 60% sodium hydride in mineral oil (0.95 g, 23.82 mmol) was added portionwise at room temperature, allowing to stir further 40 min at room temperature after the addition was finished. 1-Bromopentane (3.59 g, 23.82 mmol) was added dropwise at room temperature and the reaction mixture was stirred at room temperature for 3 hours. Reaction was stopped by the addition of water (20 ml) and then diluted with ethyl acetate (200 ml) and water (150 ml). The layers were separated and the organic layer was washed 2 more times with water (2×150 ml). The aqueous fractions were combined and extracted 3 times with ethyl acetate (3×100 ml). All the organic fractions were combined, dried over sodium sulphate and concentrated in vacuo. The residue was purified by column chromatography (silica gel, 25%-30% ethyl acetate in hexane) to give 3.77 g (64%) of 1-N-pentyl-3-(-4-methoxy-1-naphthyloyl)indole 9 as an off yellow brittle solid.

Example 23

Preparation of 4-hydroxynaphthalen-1-yl-(1-pentylindol-3-yl) methanone 10

1-N-pentyl-3-(-4-methoxy-1-naphthyloyl)indole 9 (5.55 g, 14.82 mmol) was dissolved in anhydrous dichloromethane (40 ml) and cooled at −78° C. A solution of $1NBBr_3$ (16.3 ml, 16.3 mmol) was added dropwise and once the addition was complete the reaction mixture was allowed to warm up to room temperature and was stirred at room temperature overnight. The reaction mixture was poured into a solution of 2NHCl (100 ml) and stirred for 30 min, then extracted three times with dichloromethane (3×150 ml) and the combined organic fractions were filtered through celite and washed with dichloromethane. The filtrate was dried over sodium sulphate and concentrated in vacuo. The residue was purified by column chromatography (Biotage Isolera 4, SNAP-100 g, 30%-35% ethyl acetate in heptane) to give 840 mg (16%) of 4-hydroxynaphthalen-1-yl-(1-pentylindol-3-yl) methanone 10 as a cream solid.

Example 24

Preparation of 4-(t-butyloxyacetate)naphthalen-1-yl-(1-pentylindol-3-yl) methanone 11

4-Hydroxynaphthalen-1-yl-(1-pentylindol-3-yl) methanone 10 (840 mg, 2.33 mmol) was dissolved in acetonitrile (50 ml) followed by the addition of potassium carbonate (0.98 g, 7.00 mmol) and t-butyl bromoacetate (0.68 g, 3.50 mmol). The reaction mixture was stirred at room temperature overnight. The reaction mixture was filtered and the filtrate was concentrated in vacuo. The residue was purified by column chromatography (Biotage Isolera 4, SNAP-50g, 15% ethyl acetate in hexane) to give 980 mg (92%) of 4-(t-butyloxyacetate)naphthalen-1-yl-(1-pentylindol-3-yl) methanone 11 as an orange oil.

Example 25

Preparation of 4-carboxymethylether naphthalene-1-yl-(1-pentylindol-3-yl)methanone (Hapten-D)

4-(t-butyloxyacetate)naphthalen-1-yl-(1-pentylindol-3-yl) methanone 11 (980 mg, 2.07 mmol) was dissolved in dichloromethane (30 ml) and trifluoroacetic acid (30 ml) was added and the reaction mixture was stirred for 3 hours at room temperature. The solvent was removed in vacuo and the residue was purified by column chromatography (Biotage Isolera 4, SNAP-50g, 50% ethyl acetate in hexane) to give 480 mg (44%) of 4-carboxymethylether naphthalene-1-yl-(1-pentylindol-3-yl)methanone (Hapten-D) as a white solid.
NMR $^{13}$C (DMSO, d$_7$) (δ: ppm): 189.83, 169.26, 153.99, 138.24, 136.21, 130.99, 130.88, 126.83, 126.71, 126.05, 125.20, 124.79, 124.49, 122.61, 121.69, 121.36, 121.21, 115.63, 110.35, 103.52, 63.12, 45.54, 28.56, 28.41, 21.05, 13.36.

Example 26

Conjugation of 4-carboxymethylether naphthalene-1-yl-(1-pentylindol-3-yl)methanone (Hapten-D) to BSA To a solution of 4-carboxymethylether naphthalene-1-yl-(1-pentylindol-3-yl) methanone (Hapten-D) (47.72 mg, 0.09 mM) in DMF (1.0 ml) was added N, N-dicyclohexylcarbodiimide (DCC) (20.42 mg, 0.099 mM) and N-hydroxysuccinimide (11.39 mg, 0.099 mM) and the mixture was stirred at room temperature overnight. The dicyclohexylurea formed was removed by filtration and the solution was added drop-wise to a solution of BSA (150 mg, 2.3 µM) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give 4-carboxymethylether naphthalene-1-yl-(1-pentylindol-3-yl)methanone conjugated to BSA.
MALDI results showed 18.16 molecules of Hapten-D had been conjugated to one molecule of BSA.

Example 27

Conjugation of 4-carboxymethylether naphthalene-1-yl-(1-pentylindol-3-yl)methanone (Hapten-D) to BTG (Immunogen-IV)

To a solution of 4-carboxymethylether naphthalene-1-yl-(1-pentylindol-3-yl)methanone (Hapten-D) (53.47 mg, 0.101 mM) in DMF (1.0 ml) was added N,N-dicyclohexylcarbodiimide (DCC) (22.9 mg, 0.111 mM) and N-hydroxysuccinimide (12.77 mg, 0.111 mM) and the mixture was stirred at room temperature overnight. The dicyclohexylurea formed was removed by filtration and the solution was added drop wise to a solution of BTG (150 mg) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give immunogen-IV.

Example 28

Conjugation of 4-carboxymethylether naphthalene-1-yl-(1-pentylindol-3-yl)methanone (Hapten-D) to HRP EDC hydrochloride (10 mg) was dissolved in water (0.5 ml) and immediately added to a solution of 4-carboxymethylether naphthalene-1-yl-(1-pentylindol-3-yl)methanone (Hapten-D) (2 mg) in DMF (0.2 ml). After mixing, this solution was added drop wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Figure 12:
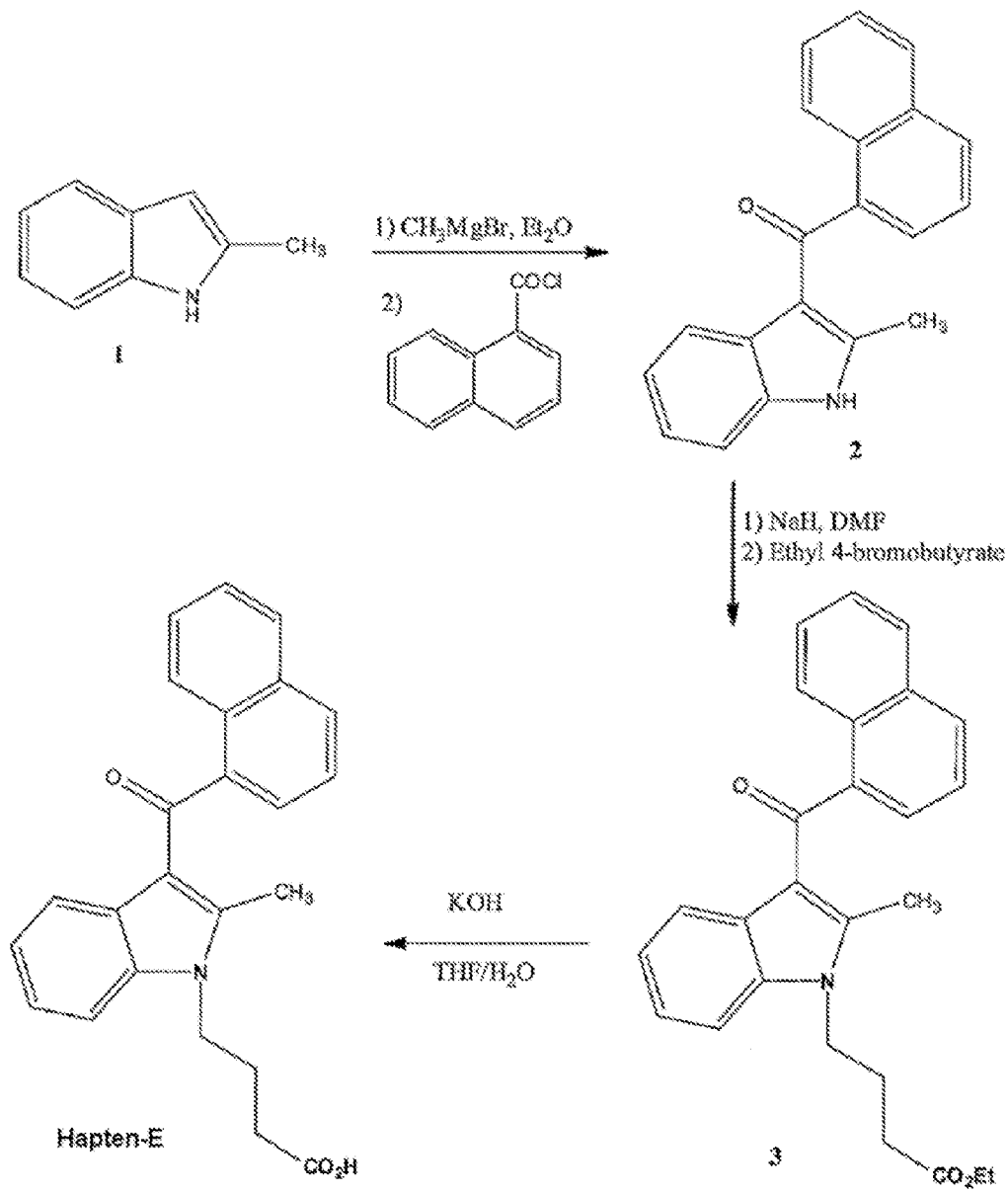
FIG. 12 contains diagrams of chemical reactions of the synthesis of Hapten-E.

Preparation of Hapten E/Immunogen VII (see FIG. 12)

Example 29

Preparation of (2-methyl-1H-indol-3-yl)(naphthalen-1-yl) methanone 2

2-Methylindole 1 (10 g, 76 3 mmol) was dissolved in diethylether (100 ml) under nitrogen atmosphere and cooled to 0° C. MeMgBr (3M) solution (26.7 ml, 80.15 mmol) was added dropwise and allowed to stir at room temperature for 3 hours. In the meantime, 1-naphthoic acid (13.13 g, 76 3 mmol) was dissolved in thionyl chloride (50 ml) and refluxed for 90 min, then the solvent was removed under vacuo and the residue was dissolved in diethylether (50 ml). The resulting solution was added dropwise to the indole reaction mixture at 0° C. and then allowed to stir at room temperature for 2 hours. A solution of ammonium chloride (200 ml) was added to the reaction mixture and the resulting mixture was stirred at room temperature overnight. The solid that was formed was collected by filtration, washed with water and hexane then dried in a dessicator over phosphorous pentoxide to give 9.7 g (45%) (2-methyl-1H-indol-3-yl)(naphthalen-1-yl) methanone 2 as a cream solid.

Example 30

Preparation of ethyl 4-(3-(1-naphthoyl)-2-methyl-1H-indol-1-yl) butanoate 3

60% Sodium hydride in mineral oil (266 mg, 6.65 mmol) was suspended in dimethylformamide (15 ml) and (2-Methyl-1H-indol-3-yl)(naphthalen-1-yl) methanone 2 (1.5 g, 5.54 mmol) was added portionwise at room temperature, allowing to stir further 30 min at room temperature after the addition was finished. Ethyl-4-bromoacetate (1.2 ml, 8.31 mmol) was added dropwise at room temperature and the reaction mixture was stirred at room temperature overnight. Solvents were removed in vacuo and the residue was partitioned between ethyl acetate (200 ml) and water (150 ml). The layers were separated and aqueous layer was extracted 2 times with ethyl acetate (2×100 ml). All the organic fractions were combined, dried over sodium sulphate and concentrated in vacuo. The residue was purified by column chromatography (silica gel, 20% ethyl acetate in hexane) to give 500 mg (23%) of ethyl 4-(3-(1-naphthoyl)-2-methyl-1H-indol-1-yl) butanoate 3 as semi-solid.

Example 31

Preparation of 4-(3-(1-naphthoyl)-2-methyl-1H-indol-1-yl)butanoic acid (Hapten-E)

Ethyl 4-(3-(1-naphthoyl)-2-methyl-1H-indol-1-yl) butanoate 3 (500 mg, 1.25 mmol) was dissolved in tertahydrofuran (5 ml) and water (5 ml) was added followed by potassium hydroxide (206 mg, 3.68 mmol). The reaction mixture was stirred at room temperature overnight. The solvent was removed in vacuo, the residue was acidified to pH3 and extracted three times with a mixture 1:1 ethyl acetate:tetrahydrofuran (3×50 ml). The organic fractions were combined, dried over sodium sulphate and concentrated under vacuo. The residue was purified by column chromatography (silica gel, ethyl acetate) to give 350 mg (75%) 4-(3-(1-naphthoyl)-2-methyl-1H-indol-1-yl)butanoic acid Hapten-E as a yellow solid.

Example 32

Conjugation of 4-(3-(1-naphthoyl)-2-methyl-1H-indol-1-yl) butanoic acid (Hapten-E) to BSA To a solution of 4-(3-(1-naphthoyl)-2-methyl-1H-indol-1-yl) butanoic acid (Hapten-E) (41.97 mg, 0.09 mM) in DMF (1.0 ml) was added N, N-dicyclohexylcarbodiimide (DCC) (28.64 mg, 0.12 mM) and N-hydroxysuccinimide (14.3 mg, 0.12 mM) and the mixture was stirred at room temperature overnight. The dicyclohexylurea formed was removed by filtration and the solution was added drop-wise to a solution of BSA (150 mg, 2.3 µM) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give 4-(3-(1-naphthoyl)-2-methyl-1H-indol-1-yl) butanoic acid (Hapten-E) conjugated to BSA.

MALDI results showed 37.64 molecules of hapten-E had been conjugated to one molecule of BSA.

Example 33

Conjugation of 4-(3-(1-naphthoyl)-2-methyl-1H-indol-1-yl) butanoic acid (Hapten-E) to BTG (Immunogen-VII)

To a solution of 4-(3-(1-naphthoyl)-2-methyl-1H-indol-1-yl) butanoic acid (Hapten-E) (50.25 mg, 0.14 mM) in DMF (1.0 ml) was added N, N-dicyclohexylcarbodiimide (DCC) (30.72 mg, 0.15 mM) and N-hydroxysuccinimide (17.13 mg, 0.15 mM) and the mixture was stirred at room temperature overnight. The dicyclohexylurea formed was removed by filtration and the solution was added drop wise to a solution of BTG (150 mg) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give immunogen-VII.

Example 34

Conjugation of 4-(3-(1-naphthoyl)-2-methyl-1H-indol-1-yl) butanoic acid (Hapten-E) to HRP EDC hydrochloride (10 mg) was dissolved in water (0.5 ml) and immediately added to a solution of 4-(3-(1-naphthoyl)-2-methyl-1H-indol-1-yl) butanoic acid (Hapten-E) (2 mg) in DMF (0.2 ml). After mixing, this solution was added drop wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Preparation of Antisera

In order to generate polyclonal antisera, each immunogen of the present invention is mixed with Freund's Adjuvant and the mixture is injected into a host animal, such as rabbit, sheep, mouse, guinea pig or horse. Sheep is the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

The specific antibodies prepared in this invention are useful as reagents in immunoassays for the detection or determination of synthetic cannabinoids and their metabolites in biological fluids.

Example 35

Preparation of Antibodies to Immunogens I, II, IV, VII and VIII

General Method:

An aqueous solution of each immunogen was formulated with Freund's Complete Adjuvant (FCA) to form an emulsion consisting of 2 mg/ml*immunogen in 50% (v/v) FCA. Three sheep were immunised with this emulsion (1° immunisation), 0.25 ml being intramuscularly injected at each of four sites in the flank of each animal. Subsequent immunizations (boosts) contained 1 mg/ml*immunogen. All boosts were emulsified in 50% (v/v) Freund's Incomplete Adjuvant (FIA) and were administered in the same manner as the 1° immunisation, at monthly intervals. Blood sampling took place 7 to 14 days after each boost. *The general procedure for immunogen administration is outlined above, however, it was necessary to deviate from this protocol in some cases, due to reduced immunogen concentrations (Immunogens II, IV, VII and VIII) and/or amount available (Immunogen VIII). Any deviations from the protocol described are outlined in Table 5 below and highlighted in bold.

TABLE 5

Amount and volume of immunogens administered for primary and subsequent boosts

| Immunogen | Primary Amount/Volume | Boost Amount/Volume |
|---|---|---|
| I | 2 mg/1 ml | 1 mg/1 ml |
| II | 2 mg/1.4 ml | 1 mg/1 ml |
| IV | 2 mg/1.3 ml | 1 mg/1 ml |
| VII | 2 mg/1.4 ml | 1 mg/1 ml |
| VIII | 1 mg/1.45 ml | 0.5 mg/1 ml |

Blood Collection

Briefly, blood is collected by applying pressure to the exposed jugular vein and inserting a clean 14 gauge hypodermic needle to remove 500 ml of blood per sheep, under gravity. The blood is stored at 37° C. for a minimum of 1 hour before the clots are separated from the side of the centrifuge bottles using disposable 1 ml pipettes (ringing). The samples are stored at 4° C. overnight.

Processing & Extraction of Immunoglobulin (Ig) Fraction:

Samples are centrifuged at 4000 g for 30 minutes at 4° C. The serum is then poured off and centrifuged again at 16,000 g for 15 minutes at 4° C., before being aliquoted and stored at <−20° C.

Precipitation of IgG from polyclonal antisera is carried out in two steps, using caprylic acid initially to precipitate most of the non-Ig G proteins, including albumin, followed by ammonium sulphate to extract IgG from the supernatant. This method produces a highly purified IgG fraction.

8 ml of 60 mM sodium acetate buffer, pH 4.4 is added to 2 ml of antisera, followed by the addition of 200 µl of caprylic acid. The resulting mixture is mixed on a roller for 30 minutes at room temperature. The precipitate is removed by centrifuging the samples at 1000 g for 20 minutes at 4° C. and filtering the supernatant through a 0.2 µm Acrodisc™ filter. 1.4 ml of 0.5M carbonate-bicarbonate buffer, pH 10.7, is added to each sample supernatant and cooled to 4° C. 9 ml of saturated ammonium sulphate solution is added slowly whilst shaking and the resulting mixture is placed on a roller for 30 minutes at room temperature. The precipitate is extracted by centrifuging the samples at 1000 g for 35 minutes at 4° C. The supernatant is poured off and the pellet re-suspended in 2 ml PBS, pH 7.2. The sample is dialysed overnight at 4° C. in PBS, pH7.2 containing 0.09% azide. After dialysis, the sample is filtered using a 0.2 µm Acrodisc™ filter and aliquoted for storage at <20° C. The IgG fraction can then be evaluated by competitive ELISA microtiter plate assay, as described below.

Example 36

Characterisation of Antibodies to Immunogens I, II, IV, VII and VIII

Standard Curves
General Method: Immunogens I and II

The wells of an enhanced binding 96 well polystyrene microtiter plate were coated with IgG fraction of antiserum raised to Immunogen I or II, diluted in 10 mM Tris, pH8.5 (125 µl/well). The appropriate antibody coating dilution was determined using standard ELISA checkerboard techniques. The plate was incubated overnight at 4° C., washed 4 times over 10 minutes with Tris buffered saline containing Tween 20 (TBST) and tapped dry. Standard solutions (JWH-018 for Immunogens I and II) were applied at 0, 0.625, 1.25, 2.5, 5, 10, 20 and 40 ng/ml and 50 µl of each was added to the appropriate wells. 75 µl of conjugate (appropriate hapten-HRP) diluted in Tris buffer (pH 7.2) containing EDTA, D-mannitol, sucrose, thimerosal and BSA, was added to each of the wells. The appropriate dilution of conjugate was also determined using standard ELISA checkerboard techniques. The plate was incubated at 25° C. for 1 hour. Excess unbound conjugate was removed by washing 6 times over a 10 minute period with TBST. 125 µl of tetramethylbenzidine (TMB) substrate solution was added to each well of the plate that was then incubated for 20 minutes in the dark at room temperature. The reaction was terminated by addition of 125 µl 0.2M $H_2SO_4$ to each well. The absorbance was then measured at 450 nm using a microtiter plate reader. The data are inputted to a computer program called 'KC Junior'. It is a 4 parameter fit curve and allow the calculation of concentrations between the standard runs. This program is used to calculate the IC50s by dividing the 0 ng/ml OD value by 2 and obtaining the concentration value from the curve for this OD. The data generated in the assay and inputted to a computer program called 'KC Junior' are presented in Tables 7, 8 and 9.

General Method: Immunogens I and II

In a similar manner to that described above, the wells of a 96-well microtiter plate were coated with the IgG fraction of the antiserum raised to Immunogens I or II. Standard solutions (JWH-018 for Immunogen I and II) were applied at 0, 0.625, 1.25, 2.5, 5, 10, 20 and 40 ng/ml and conjugate was employed as detection reagent. The data generated are presented in Table 7.

General Method: Immunogens IV, VII, VIII

In a similar manner to that described above, the wells of a 96-well microtiter plate were coated with the IgG fraction of the antiserum raised to Immunogens IV, VII or VIII. Standard solutions (JWH-018 for Immunogens IV and VIII, JWH-015 for Immunogen VII) were prepared in TBST at 0, 1.25, 2.5, 5, 10, 20, 40 and 80 ng/ml and conjugate was employed as detection reagent. The data generated are presented in Tables 8 and 9.

The data set out in Tables 7-10 are generated using antibodies raised against the indicated Immunogens in a competitive binding assay with the indicated tracers, using the indicated standards

TABLE 6

| Immunogen/Hapten | Antibody | Standard | Tracer/hapten |
|---|---|---|---|
| Immunogen I | CJ-5-68/LK955 | RS1803B12 | JWH-018 | ESC4962/LK962 |
| Immunogen II | CJ-5-56/LK959 | RS1833B12 | JWH-018 | ESC4555/LK959 |
| Immunogen IV | CJ-7-04/LK1122 | RS2142B5 | JWH-018 | ESC5913/LK1122 |
| Immunogen VII | CJ-7-178/LK1199 | RS2255B1 | JWH-015 | ESC6616/LK1199 |
| Immunogen VIII | CJ-6-45/LK1037 | RS2099B5 | JWH-018 | ESC5794/LK1108 |

Figure 13:
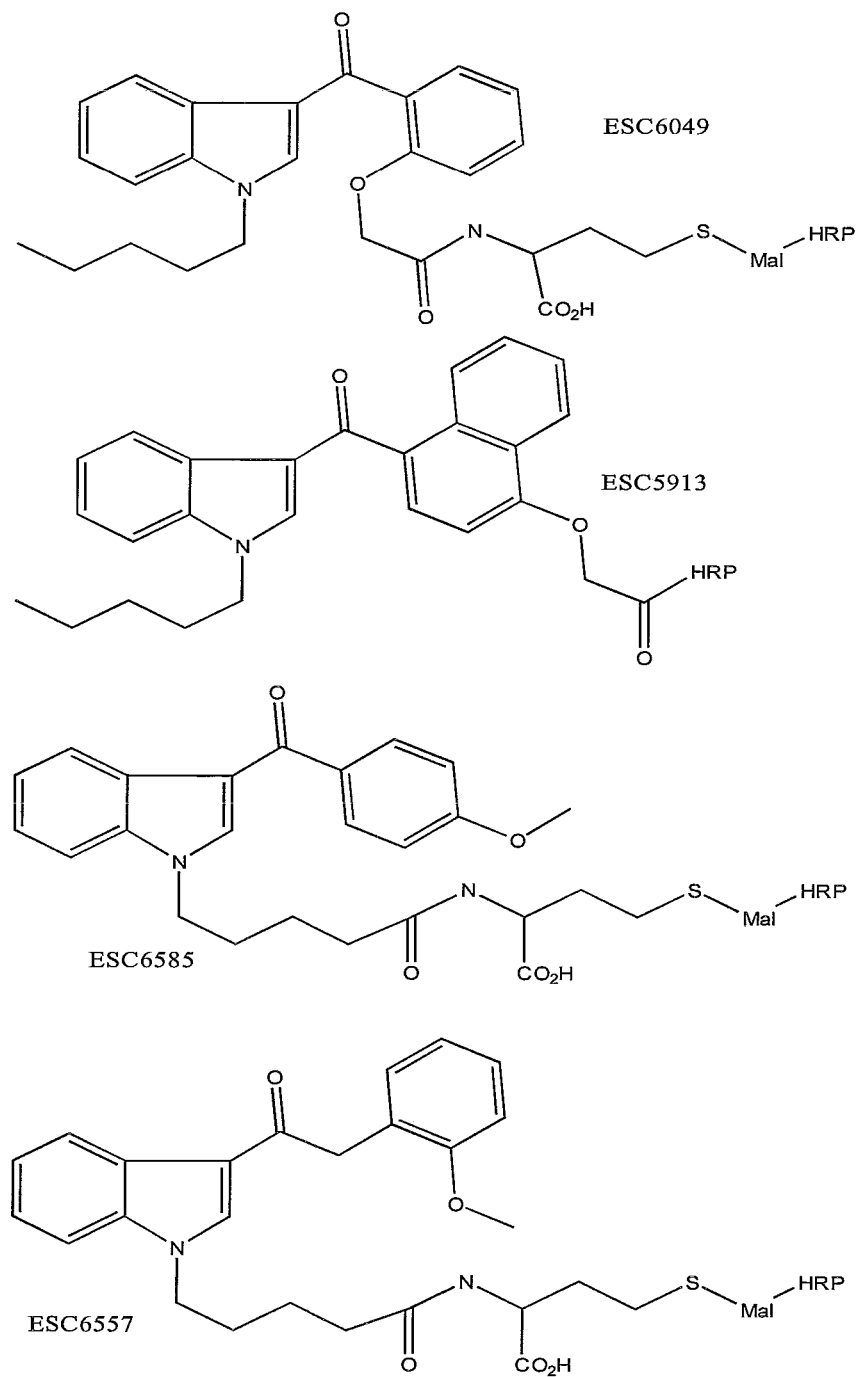
FIG. 13 contains diagrams of Tracers used in the invention.
Figure 13:
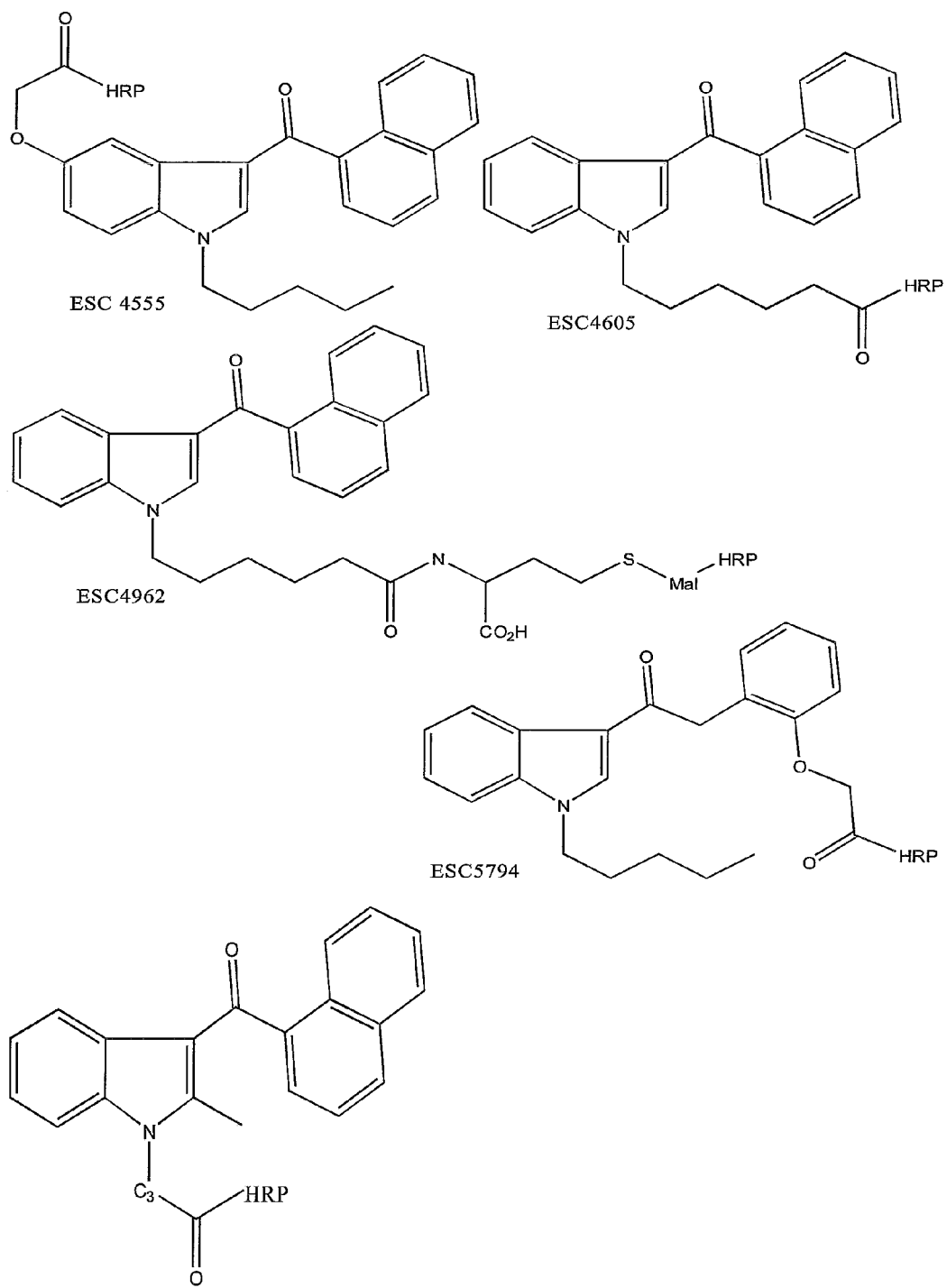
Figure 14:
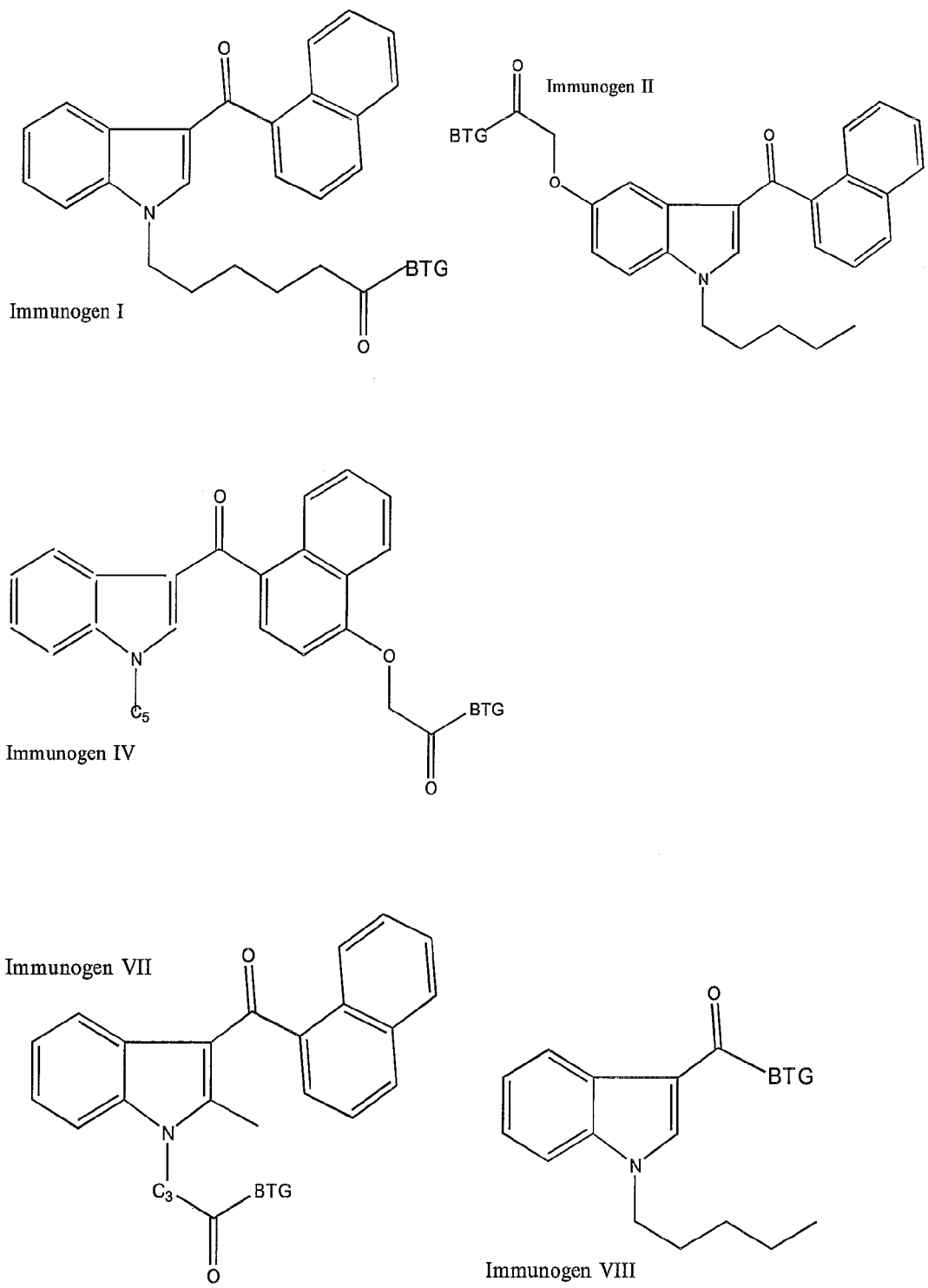
FIG. 14 contains diagrams of Immunogens of the invention.

The tracers are illustrated in FIG. 13 and the Immunogens in FIG. 14.

Tables 7, 8 and 9: Data generated from competitive microtiter plate assays for Synthetic Cannabinoids and their metabolites, employing antisera generated to Immunogens I, II, IV, VII and VIII

TABLE 7

| | Antibody to Immunogen I | |
|---|---|---|
| JWH-018 ng/ml | $A_{450}$ | % $B/B_0$ |
| 0 | 1.61 | 100 |
| 0.625 | 1.247 | 77 |
| 1.25 | 1.004 | 62 |
| 2.5 | 0.707 | 44 |
| 5 | 0.504 | 31 |
| 10 | 0.323 | 20 |
| 20 | 0.22 | 14 |
| 40 | 0.15 | 9 |
| $IC_{50}$ (ng/ml) | | 2.016 |

TABLE 7-continued

| JWH-018 ng/ml | Antibody to Immunogen II | |
|---|---|---|
| | A450 | % B/B0 |
| 0 | 1.4575 | 100 |
| 0.625 | 0.984 | 68 |
| 1.25 | 0.7685 | 53 |
| 2.5 | 0.499 | 34 |
| 5 | 0.3615 | 25 |
| 10 | 0.2525 | 17 |
| 20 | 0.1855 | 13 |
| 40 | 0.149 | 10 |
| $IC_{50}$ (ng/ml) | 1.333 | |

TABLE 8

| JWH-018 ng/ml | Antibody to Immunogen IV | |
|---|---|---|
| | A450 | % B/B0 |
| 0 | 1.6985 | 100 |
| 1.25 | 1.479 | 87 |
| 2.5 | 1.1625 | 68 |
| 5 | 0.7155 | 42 |
| 10 | 0.442 | 26 |
| 20 | 0.2645 | 16 |
| 40 | 0.1735 | 10 |
| 80 | 0.116 | 7 |
| IC50 (ng/ml) | 4.133 | |

TABLE 9

| JWH-015 ng/ml | Antibody to Immunogen VII | | JWH-018 ng/ml | Antibody to Immunogen VIII | |
|---|---|---|---|---|---|
| | A450 | % B/B0 | | A450 | % B/B0 |
| 0 | 2.035 | 100 | 0 | 1.3825 | 100 |
| 1.25 | 1.53 | 75 | 1 | 1.09 | 79 |
| 2.5 | 1.2605 | 62 | 3 | 0.8765 | 63 |
| 5 | 1.0875 | 54 | 5 | 0.708 | 51 |
| 10 | 0.869 | 43 | 10 | 0.5515 | 40 |
| 20 | 0.69 | 34 | 20 | 0.4015 | 29 |
| 40 | 0.5345 | 26 | 40 | 0.3095 | 22 |
| 80 | 0.407 | 20 | 80 | 0.217 | 16 |
| IC50 (ng/ml) | 5.910 | | IC50 (ng/ml) | 5.230 | |

$A_{450}$=absorbance at 450 nm
B=absorbance at 450 nm at xng/ml standard concentration
$B_0$=absorbance at 450 nm at 0 ng/ml standard concentration
$IC_{50}$=standard concentration which produces 50% $B/B_0$ Cross Reactivity In order to determine the specificity of the competitive ELISAs, standard solutions of a range of structurally similar synthetic cannabinoids and their metabolites were prepared in TBST.

Using the calibration curves generated and employing a single level of cross reactants, these were used to determine the cross-reactivity of each immunoassay with these substances. The results of this study are presented in Table 10, as % $B/B_0$. These are the standards used for the $IC_{50}$ and cross-reactivity data generation:

Immunogen I—JWH-018
Immunogen II—JWH-018
Immunogen IV—JWH-018
Immunogen VII—JWH-015
Immunogen VIII—JWH-018

TABLE 10

Cross reactivity of the competitive ELISAs for synthetic cannabinoids and their metabolites

| | Cross-reactants at 100 ng/ml; 1000 ng/ml | Antibody to Immunogen I % B/B0 | Antibody to Immunogen II %B/B0 | Antibody to Immunogen IV % B/B0 | Antibody to Immunogen VII % B/B0 | Antibody to Immunogen VIII % B/B0 |
|---|---|---|---|---|---|---|
| 1 | JWH-018 | 5.19 | 9.29 | 6.80 | 67.66 | 17.66 |
| 2 | 2-OH JWH-018 (JWH-018 2-hydroxyindole metabolite) | 95.37 | | 100.14 | 95.08 | 101.36 |
| 3 | 4-OH JWH-018 (JWH-018 4-hydroxyindole metabolite) | 46.39 | 29.49 | 20.42 | 89.96 | 16.72 |
| 4 | 5-OH JWH-018 (JWH-018 5-hydroxyindole metabolite) | 11.79 | 12.14 | 78.56 | 85.76 | 87.67 |
| 5 | 6-OH JWH-018 (JWH-018 6-hydroxyindole metabolite) | 8.07 | 24.39 | 51.00 | 68.17 | 89.86 |
| 6 | 7-OH JWH-018 (JWH-018 7-hydroxyindole metabolite) | 6.72 | 34.79 | 93.31 | 68.53 | 94.46 |
| 7 | N-desalkyl JWH-018: LK1012 10CD194 | 15.63 | 99.18 | 95.55 | 80.08 | 90.49 |
| 8 | (±)-JWH 018 N-(4-hydroxypentyl) metabolite | 4.23 | 53.99 | 52.29 | 57.37 | 21.94 |
| 9 | JWH-018 N-(5-hydroxypentyl) metabolite | 3.50 | 53.38 | 78.42 | 53.32 | 57.37 |
| 10 | JWH-018 N-pentanoic acid metabolite | 4.51 | 85.61 | 99.89 | 53.02 | 100.31 |
| 11 | JWH 018 N-(1,2-dimethylpropyl) isomer | 6.60 | 71.33 | 87.11 | 62.29 | 67.71 |
| 12 | JWH 018 2'-naphthyl isomer | 75.90 | | 28.13 | 94.98 | 14.94 |
| 13 | JWH 018 adamantyl analog | 95.94 | | 99.02 | 94.48 | 10.97 |
| 14 | JWH-018 N-(1-methylbutyl) isomer | 12.42 | 51.92 | 73.49 | 67.71 | 63.22 |
| 15 | JWH-018 N-(2,2-dimethylpropyl) isomer | 3.89 | 60.15 | 80.42 | 52.46 | 95.09 |
| 16 | JWH-018 6-methoxyindole analogue | 10.55 | 20.44 | 90.65 | 72.33 | 77.22 |
| 17 | JWH-018 N-(2-methylbutyl) isomer | 3.61 | 28.60 | 29.88 | 58.84 | 85.16 |
| 18 | JWH 018 N-(3-methylbutyl) isomer | 3.16 | 30.38 | 12.75 | 48.81 | 53.29 |
| 19 | JWH-073 | 3.56 | 15.24 | 13.63 | 58.34 | 25.50 |
| 20 | 2-OH JWH-073 (JWH-073 2-hydroxyindole metabolite) | 89.62 | | 89.63 | 92.65 | 93.42 |
| 21 | 4-OH JWH-073 (JWH-073 4-hydroxyindole metabolite) | 39.50 | 40.14 | 28.69 | 82.82 | 26.23 |
| 22 | 5-OH JWH-073 (JWH-073 5-hydroxyindole metabolite) | 7.34 | 20.73 | 84.06 | 75.11 | 90.70 |
| 23 | 6-OH JWH-073 (JWH-073 6-hydroxyindole metabolite) | 5.93 | 28.03 | 74.89 | 61.83 | 93.52 |
| 24 | 7-OH JWH-073 (JWH-073 7-hydroxyindole metabolite) | 5.59 | 46.05 | 96.95 | 61.78 | 94.04 |
| 25 | JWH-073 N-(3-hydroxybutyl) metabolite | 3.10 | 54.52 | 53.52 | 43.39 | 94.04 |

TABLE 10-continued

Cross reactivity of the competitive ELISAs for synthetic cannabinoids and their metabolites

| Cross-reactants at 100 ng/ml; 1000 ng/ml | Antibody to Immunogen I % B/B0 | Antibody to Immunogen II %B/B0 | Antibody to Immunogen IV % B/B0 | Antibody to Immunogen VII % B/B0 | Antibody to Immunogen VIII % B/B0 |
|---|---|---|---|---|---|
| 26 JWH-073 N-(4-hydroxybutyl) metabolite | 3.22 | 60.01 | 52.61 | 48.81 | 57.99 |
| 27 JWH-073 N-butanoic acid metabolite | 6.88 | 92.20 | 98.95 | 60.01 | 94.98 |
| 28 JWH 073 2-methylnaphthyl analog | 21.84 | 43.34 | 34.47 | 76.74 | 78.79 |
| 29 JWH-073 4-methylnaphthyl analogue | 45.54 | | 7.01 | 78.36 | 19.75 |
| 30 JWH-007 | 32.96 | 66.06 | 60.63 | 27.77 | 61.76 |
| 31 JWH-011 | 62.13 | | 99.19 | 57.43 | 97.49 |
| 32 JWH-015 | 14.67 | 65.67 | 93.20 | 17.84 | 92.27 |
| 33 JWH-016 | 20.71 | 68.73 | 91.14 | 19.31 | 75.24 |
| 34 JWH-019 | 7.22 | 15.42 | 21.96 | 70.05 | 74.50 |
| 35 JWH 019 5-hydroxyindole metabolite (JWH-019-M2) | 19.81 | 17.34 | 93.84 | 87.58 | 101.57 |
| 36 JWH-020 | 16.03 | 35.75 | 73.73 | 81.30 | 100.73 |
| 37 JWH-022 | 4.51 | 11.72 | 10.61 | 58.44 | 28.94 |
| 38 JWH-030 | 61.17 | | 93.17 | 89.66 | 94.25 |
| 39 JWH-081 | 62.13 | | 3.78 | 86.72 | 15.88 |
| 40 JWH-081 2-methoxynaphthyl isomer or (JWH-267) | 69.58 | | 27.67 | 83.43 | 58.20 |
| 41 JWH-081 5-methoxynaphthyl isomer | 18.51 | 60.90 | 6.24 | 94.16 | 26.56 |
| 42 JWH-081 7-methoxynaphthyl isomer (JWH-164) | 88.26 | | 39.20 | 97.60 | 59.51 |
| 43 JWH-081 N-(5-hydroxypentyl) metabolite | 61.86 | | 26.31 | 89.31 | 47.16 |
| 44 JWH-098 | 77.58 | | 44.03 | 82.85 | 59.80 |
| 45 JWH-122 | 62.98 | 44.55 | 3.94 | 89.37 | 14.43 |
| 46 JWH 122 6-methylnaphthyl isomer | 12.55 | 39.17 | 8.12 | 86.66 | 20.46 |
| 47 JWH 122 7-methylnaphthyl isomer | 36.46 | 38.28 | 13.48 | 92.44 | 38.48 |
| 48 JWH 122 2-methylnaphthyl isomer | 33.35 | 27.14 | 26.13 | 85.37 | 61.74 |
| 49 JWH-122 N-(5-hydroxypentyl) metabolite | 42.80 | 71.76 | 25.72 | 83.65 | 48.67 |
| 50 JWH-133 | 100.56 | | 98.18 | 101.84 | 100.00 |
| 51 JWH-147 | 83.85 | | 97.00 | 99.32 | 92.32 |
| 52 JWH-164 (JWH-081 7-methoxynaphthyl isomer) | 91.86 | | 36.14 | 96.13 | 57.93 |
| 53 JWH-182 | 107.08 | | 12.83 | 98.40 | 30.65 |
| 55 JWH-200 4-hydroxyindole metabolite | 44.97 | 78.17 | 87.88 | 91.15 | 91.82 |
| 56 JWH-200 5-hydroxyindole metabolite | 12.61 | 64.99 | 97.53 | 82.42 | 90.88 |
| 57 JWH-200 6-hydroxyindole metabolite | 7.27 | 61.65 | 94.41 | 65.52 | 83.20 |
| 58 JWH-200 2′-naphthyl isomer | 28.57 | | 92.29 | 94.65 | 96.12 |
| 59 JWH-201 | 77.14 | | 59.03 | 100.25 | 8.26 |
| 60 JWH-203 | 72.55 | | 52.15 | 99.08 | 9.19 |
| 61 JWH 203 3-chloro isomer (JWH-237) | 95.59 | | 55.09 | 97.42 | 10.34 |
| 62 JWH-206 (JWH-203 4-chloro isomer) | 75.96 | | 65.63 | 97.17 | 10.55 |
| 63 JWH-210 | 91.18 | | 5.53 | 96.62 | 16.87 |
| 64 JWH-210 2-ethylnaphthyl isomer | 81.37 | | 53.97 | 96.13 | 73.51 |
| 65 JWH-210 7-ethylnaphthyl isomer or JWH-234 | 73.11 | | 27.07 | 100.55 | 50.90 |
| 66 JWH-210 N-(5-carboxypentyl) metabolite | 76.77 | | 85.29 | 96.07 | 96.27 |
| 67 JWH-210 5-hydroxyindole metabolite | 83.29 | | 48.91 | 100.43 | 87.72 |
| 68 JWH-250 | 78.94 | | 41.08 | 97.23 | 9.40 |
| 69 JWH 250 N-(5-hydroxypentyl) metabolite | 75.47 | | 76.22 | 96.13 | 42.79 |
| 70 JWH 250 N-(5-carboxypentyl) metabolite | 86.21 | | 89.88 | 97.60 | 89.30 |
| 71 JWH 250 5-hydroxyindole metabolite | 100.75 | | 84.05 | 99.88 | 67.19 |
| 72 JWH-251 | 68.01 | | 42.02 | 96.74 | 9.12 |
| 73 JWH 251 3-methylphenyl isomer | 85.90 | | 51.15 | 99.32 | 8.97 |
| 74 JWH-302 | 84.66 | | 45.67 | 104.92 | 7.97 |
| 75 JWH-398 | 60.31 | 30.31 | 6.00 | 94.47 | 18.66 |
| 76 JWH-398 5-chloronaphthyl isomer | 35.53 | 23.50 | 7.06 | 91.33 | 19.67 |
| 77 JWH-398 N-(5-hydroxypentyl) metabolite | 48.07 | 67.49 | 22.01 | 82.97 | 51.33 |
| 78 AM-630 (other name 6-Iodopravadoline) | 91.12 | | 90.17 | 99.88 | 89.88 |
| 79 AM-694 | 12.17 | 36.18 | 11.30 | 75.66 | 11.92 |
| 80 AM-694 3-iodo isomer | 31.37 | 48.58 | 37.20 | 89.49 | 12.71 |
| 81 AM-694 4-iodo isomer | 73.79 | | 27.66 | 98.71 | 13.42 |
| 82 AM-1220 | 4.45 | 77.46 | 86.93 | 49.71 | 106.65 |
| 84 AM-1241 | 85.61 | | 91.38 | 94.96 | 102.46 |
| 85 AM-2201 | 3.72 | 11.72 | 6.20 | 55.28 | 16.74 |
| 86 AM-2201 N-(4-fluoropentyl) isomer | 3.45 | 14.60 | 5.72 | 52.70 | 15.00 |
| 87 AM-2201 N-(4-hydroxypentyl) metabolite | 3.80 | 46.55 | 43.62 | 52.75 | 36.41 |
| 88 AM-2233 | 16.97 | 86.43 | 92.10 | 72.46 | 91.25 |
| 89 CP-49,497-C7 ((+−) CP 47,497) | 101.20 | | 96.84 | 94.23 | 86.95 |
| 90 CP-47,497-para-quinone analogue | 100.26 | | 97.33 | 93.29 | 88.11 |
| 91 CP-49,497-C8-homologue ((+− CP) 47,497-C8-homologue) | 101.11 | | 94.66 | 98.55 | 104.88 |
| 92 ((+−)-CP 55,940) | 100.61 | | 94.60 | 100.25 | 100.25 |
| 93 (−)-CP 55,940 | 98.27 | | 93.02 | 101.15 | 97.58 |
| 94 (+)-CP 55,940 | 103.25 | | 91.38 | 97.15 | 95.12 |
| 95 HU-210 | 102.57 | | 92.53 | 100.39 | 93.42 |
| 96 HU-211 (Dexanabinol) | 103.36 | | 93.37 | 96.78 | 92.70 |
| 97 HU-308 | 101.35 | | 94.03 | 95.95 | 89.77 |
| 98 RCS-4 | 80.46 | | 19.21 | 93.51 | 5.93 |
| 99 RCS-4 2-methoxy isomer | 29.14 | 42.74 | 15.28 | 87.27 | 29.32 |

TABLE 10-continued

Cross reactivity of the competitive ELISAs for synthetic cannabinoids and their metabolites

| Cross-reactants at 100 ng/ml; 1000 ng/ml | Antibody to Immunogen I % B/B0 | Antibody to Immunogen II %B/B0 | Antibody to Immunogen IV % B/B0 | Antibody to Immunogen VII % B/B0 | Antibody to Immunogen VIII % B/B0 |
|---|---|---|---|---|---|
| 100 RCS-4 3-methoxy isomer | 31.19 | | 25.65 | 94.72 | 10.95 |
| 101 RCS-4-C4 homologue (BTM-4, SR-19, OBT-199, E-4) | 76.27 | | 27.17 | 100.20 | 9.54 |
| 102 RCS-4 N-(4-hydroxypentyl) metabolite | 65.71 | | 59.16 | 95.72 | 8.89 |
| 103 RCS-4 N-(5-hydroxypentyl) metabolite | 59.51 | | 61.03 | 94.55 | 19.13 |
| 104 RCS-4 N-(5-carboxypentyl) metabolite | 77.12 | | 91.44 | 94.00 | 91.97 |
| 105 RCS-8 (SR-18) | 82.65 | | 85.50 | 94.57 | 88.79 |
| 106 RCS-8 3-methoxy isomer | 93.24 | | 89.43 | 93.73 | 83.62 |
| 107 RCS-8 4-methoxy isomer | 94.94 | | 90.78 | 98.21 | 100.72 |
| 108 (+)WIN 55212-2 (mesylate) | 17.00 | 83.87 | 92.76 | 24.08 | 107.12 |
| 109 Win 55,212-3 mesylate | 34.00 | | 94.57 | 32.31 | 101.30 |
| 110 WIN-48,098 (other name Pravadoline) | 90.05 | | 91.64 | 92.41 | 97.90 |
| 111 WIN 55,225 (other name JWH-200) | 3.51 | 54.02 | 77.08 | 42.85 | 98.81 |
| 112 Delta 9 THC | 102.66 | | 93.62 | 96.76 | 96.10 |
| 113 Indole-3-carboxylic Acid | 101.26 | | 93.42 | 96.90 | 96.28 |
| 114 Cannabinol | 86.60 | | 94.74 | 95.43 | 94.03 |
| 115 5-hydroxyindole-3-acetic acid (5-HIAA) | 98.71 | | 96.61 | 99.46 | 108.24 |
| 116 Serotonin HCl | 99.65 | | 95.40 | 99.83 | 100.36 |
| 117 5-hydroxytryptophol | 93.30 | | 94.51 | 98.45 | 102.93 |
| 118 (−)-11-nor-9-Carboxy-delta9-THC | 100.47 | | 93.08 | 98.72 | 103.36 |

TABLE 11

| Cross-Reactant | CAS Registry Number |
|---|---|
| JWH-018 | 209414-07-3 |
| 2-OH JWH-018 (JWH-018 2-hydroxyindole metabolite) | |
| 4-OH JWH-018 (JWH-018 4-hydroxyindole metabolite) | |
| 5-OH JWH-018 (JWH-018 5-hydroxyindole metabolite) | 335161-21-2 |
| 6-OH JWH-018 (JWH-018 6-hydroxyindole metabolite) | |
| 7-OH JWH-018 (JWH-018 7-hydroxyindole metabolite) | |
| N-desalkyl JWH-018: LK1012 10CD194 | |
| (±)-JWH 018 N-(4-hydroxypentyl) metabolite | |
| JWH-018 N-(5-hydroxypentyl) metabolite | |
| JWH-018 N-pentanoic acid metabolite | |
| JWH 018 N-(1,2-dimethylpropyl) isomer | |
| JWH 018 2'-naphthyl isomer | 1131605-25-8 |
| JWH 018 adamantyl analog | |
| JWH-018 N-(1-methylbutyl) isomer | |
| JWH-018 N-(2,2-dimethylpropyl) isomer | |
| JWH-018 6-methoxyindole analogue | |
| JWH-018 N-(2-methylbutyl) isomer (JWH-073 2-methylbutyl homologue) | |
| JWH 018 N-(3-methylbutyl) isomer (JWH-073 3-methylbutyl homologue) | |
| JWH-073 | 208987-48-8 |
| 2-OH JWH-073 (JWH-073 2-hydroxyindole metabolite) | |
| 4-OH JWH-073 (JWH-073 4-hydroxyindole metabolite) | |
| 5-OH JWH-073 (JWH-073 5-hydroxyindole metabolite) | |
| 6-OH JWH-073 (JWH-073 6-hydroxyindole metabolite) | |
| 7-OH JWH-073 (JWH-073 7-hydroxyindole metabolite) | |
| JWH-073 N-(3-hydroxybutyl) metabolite | |
| JWH-073 N-(4-hydroxybutyl) metabolite | |
| JWH-073 N-butanoic acid metabolite | |
| JWH 073 2-methylnaphthyl analog | |
| JWH-073 4-methylnaphthyl analogue | |
| JWH-007 | 155471-10-6 |
| JWH-011 | 155471-13-9 |
| JWH-015 | 155471-08-2 |
| JWH-016 | 155471-09-3 |
| JWH-019 | 209414-08-4 |
| JWH 019 5-hydroxyindole metabolite (JWH-019-M2) | |
| JWH-020 | 209414-09-5 |
| JWH-022 | 209414-16-4 |
| JWH-030 | 162934-73-8 |
| JWH-081 | 210179-46-7 |
| JWH-081 2-methoxynaphthyl isomer or (JWH-267) | 824960-76-1 |
| JWH-081 5-methoxynaphthyl isomer | |
| JWH-081 7-methoxynaphthyl isomer (JWH-164) | 824961-61-7 |
| JWH-081 N-(5-hydroxypentyl) metabolite | |
| JWH-098 | 316189-74-9 |
| JWH-122 | 619294-47-2 |
| JWH 122 6-methylnaphthyl isomer | |
| JWH 122 7-methylnaphthyl isomer | 824960-56-7 |
| JWH-122 2-methylnaphthyl isomer | |
| JWH-122 N-(5-hydroxypentyl) metabolite | |
| JWH-133 | 259869-55-1 |
| JWH-147 | 914458-20-1 |
| JWH-164 (JWH-081 7-methoxynaphthyl isomer) | 824961-61-7 |
| JWH-182 | 824960-02-3 |
| JWH-200 4-hydroxyindole metabolite | |
| JWH-200 5-hydroxyindole metabolite | |
| JWH-200 6-hydroxyindole metabolite | |
| JWH-200 2'-naphthyl isomer | 133438-66-1 |
| JWH-201 | 864445-47-6 |
| JWH-203 | 864445-54-5 |
| JWH 203 3-chloro isomer (JWH-237) | 864445-56-7 |
| JWH-206 (JWH-203 4-chloro isomer) | 864445-58-9 |
| JWH-210 | 824959-81-1 |
| JWH-210 2-ethylnaphthyl isomer | |
| JWH-210 7-ethylnaphthyl isomer or JWH-234 | 824960-64-7 |
| JWH-210 N-(5-carboxypentyl) metabolite | |
| JWH-210 5-hydroxyindole metabolite | |
| JWH-250 | 864445-43-2 |
| JWH 250 N-(5-hydroxypentyl) metabolite | |
| JWH 250 N-(5-carboxypentyl) metabolite | |
| JWH 250 5-hydroxyindole metabolite | |
| JWH-251 | 864445-39-6 |
| JWH 251 3-methylphenyl isomer | |
| JWH-302 | 864445-45-4 |
| JWH-398 | 1292765-18-4 |
| JWH-398 5-chloronaphthyl isomer | |
| JWH-398 N-(5-hydroxypentyl) metabolite | |
| AM-630 (other name 6-Iodopravadoline) | 164178-33-0 |
| AM-694 | 335161-03-0 |
| AM-694 3-iodo isomer | |
| AM-694 4-iodo isomer | |
| AM-1220 | 137642-54-7 |
| AM-1241 | 444912-48-5 |
| AM-2201 | 335161-24-5 |
| AM-2201 N-(4-fluoropentyl) isomer | |
| AM-2201 N-(4-hydroxypentyl) metabolite | |
| AM-2233 | 444912-75-8 |

TABLE 11-continued

| Cross-Reactant | CAS Registry Number |
|---|---|
| CP-49,497-C7 ((+−) CP 47,497) | |
| CP-47,497-para-quinone analogue | |
| CP-49,497-C8-homologue ((+−CP) 47,497-C8-homologue) | |
| ((+−)-CP 55,940) | |
| (−)-CP 55,940 | |
| (+)-CP 55,940 | |
| HU-210 | |
| HU-211 (Dexanabinol) | |
| HU-308 | |
| RCS-4 | 1345966-78-0 |
| RCS-4 2-methoxy isomer | |
| RCS-4 3-methoxy isomer | |
| RCS-4-C4 homologue (BTM-4, SR-19, OBT-199, E-4) | |
| RCS-4 N-(4-hydroxypentyl) metabolite | |
| RCS-4 N-(5-hydroxypentyl) metabolite | |
| RCS-4 N-(5-carboxypentyl) metabolite | |
| RCS-8 (SR-18) | 1345970-42-4 |
| RCS-8 3-methoxy isomer | |
| RCS-8 4-methoxy isomer | |
| (+)WIN 55212-7 (mesylate) | 131543-23-2 |
| Win 55,212-3 mesylate | 131543-25-4 |
| WIN-48,098 (other name Pravadoline) | 92623-83-1 |
| WIN 55,225 (other name JWH-200) | 103610-04-4 |
| Delta 9 THC | 1972-08-3 |
| Indole-3-carboxylic Acid | 87-51-4 |
| Cannabinol | 521-35-7 |
| 5-hydroxyindole-3-acetic acid (5-HIAA) | 54-16-0 |
| Serotonin HCl | 153-98-0 |
| 5-hydroxytryptophol | 154-02-9 |
| (−)-11-nor-9-Carboxy-delta9-THC | 56354-06-4 |

The invention claimed is:

1. An antibody that binds to structure:

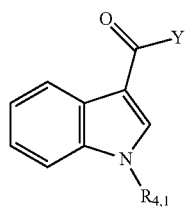

wherein $R_{4,1}$ is a $C_4$ or $C_5$, substituted or unsubstituted, saturated or unsaturated, hydrocarbon chain; and, Y is substituted or unsubstituted naphthyl or substituted phenyl; and, wherein the antibody has a cross-reactivity presented as $B/B_0\%$ of $\leq 15\%$ (standardised with JWH-018 and using tracer ESC5913, wherein JWH-018 is

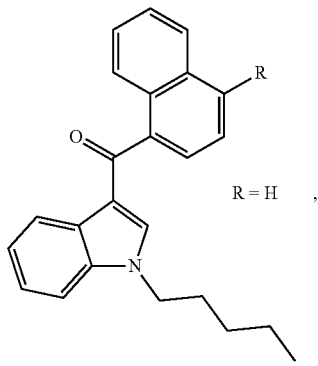

R = H, wherein ESC5913 is

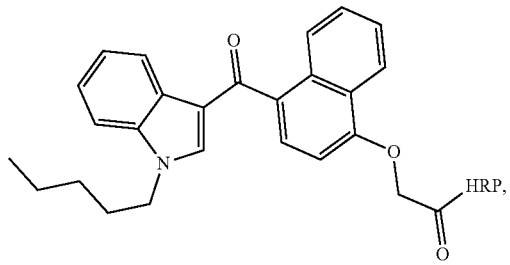

HRP, and wherein HRP is Horse Radish Peroxidase)

against each one of the cross-reactants selected from the group consisting of JWH-018, JWH-018 (N-(3-methylbutyl) isomer, JWH-073, JWH-073 4-methylnaphthyl analogue, JWH-022, JWH-081, JWH-081 5-methoxynaphthyl isomer, JWH-122, JWH-122 6-methylnaphthyl isomer, JWH-122 7-methylnaphthyl isomer, JWH-182, JWH-210, JWH-398, JWH-398 5-chloronaphthyl isomer, AM-694, AM-2201, and AM-2201 N-(4-fluoropentyl) isomer, at a cross-reactant concentration of 100 ng/ml, wherein $B_0$ is absorbance at 450 nm at zero ng/ml standard concentration, and wherein B is absorbance at 450 nm at predetermined standard concentrations.

* * * * *